(12) United States Patent
Körbelin et al.

(10) Patent No.: US 10,287,318 B2
(45) Date of Patent: May 14, 2019

(54) VIRAL VECTOR FOR THE TARGETED TRANSFER OF GENES IN THE BRAIN AND SPINAL CORD

(71) Applicant: Boehringer Ingelheim International GmbH, Ingelheim am Rhein (DE)

(72) Inventors: Jakob Körbelin, Hamburg (DE); Stefan Michelfelder, Freiburg (DE); Martin Trepel, Hamburg (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/303,950

(22) PCT Filed: Apr. 15, 2015

(86) PCT No.: PCT/EP2015/058123
§ 371 (c)(1),
(2) Date: Oct. 13, 2016

(87) PCT Pub. No.: WO2015/158749
PCT Pub. Date: Oct. 22, 2015

(65) Prior Publication Data
US 2017/0029464 A1    Feb. 2, 2017

(30) Foreign Application Priority Data
Apr. 17, 2014 (DE) .......................... 10 2014 207 498

(51) Int. Cl.
| | | |
|---|---|---|
| *A61K 38/00* | (2006.01) | |
| *C07K 7/06* | (2006.01) | |
| *C07K 14/075* | (2006.01) | |
| *C07K 14/005* | (2006.01) | |
| *C12N 7/00* | (2006.01) | |
| *C12N 15/86* | (2006.01) | |
| *A61K 48/00* | (2006.01) | |

(52) U.S. Cl.
CPC .............. *C07K 7/06* (2013.01); *C07K 14/005* (2013.01); *C12N 7/00* (2013.01); *C12N 15/86* (2013.01); *A61K 38/00* (2013.01); *A61K 48/00* (2013.01); *C12N 2710/14144* (2013.01); *C12N 2750/14122* (2013.01); *C12N 2750/14133* (2013.01); *C12N 2750/14143* (2013.01); *C12N 2810/6027* (2013.01)

(58) Field of Classification Search
None
See application file for complete search history.

(56) References Cited

U.S. PATENT DOCUMENTS

| | | | |
|---|---|---|---|
| 7,314,974 B2 * | 1/2008 | Cao ..................... | C07K 14/195 800/289 |
| 8,007,780 B2 | 8/2011 | Arbetman et al. | |
| 2007/0061916 A1* | 3/2007 | Kovalic ............... | C07K 14/415 800/278 |
| 2007/0172460 A1 | 7/2007 | Kleinschmidt et al. | |

FOREIGN PATENT DOCUMENTS

| | | |
|---|---|---|
| DE | 102014207498 | 10/2015 |
| WO | 2004/083441 A2 | 9/2004 |
| WO | 2010127097 | 11/2010 |
| WO | 2015158749 | 10/2015 |

OTHER PUBLICATIONS

Search Report and Written Opinion in related PCT Patent Application Serial No. PCT/EP2015/058123 dated Dec. 11, 2015, 17 pages (translation attached).
Allard, et al., "Characterization of rat spinal cord receptors to FLFQPQRFamide, a mammalian morphine modulating peptide: a binding study", Brain Res., Oct. 23, 1989, vol. 500, issue 1-2, pp. 169-176, Abstract Only.
Benyhe, et al., "Met-5-enkephalin-Arg-6-Phe-7, an endogenous neuropeptide, binds to multiple opioid and nonopioid sites in rat brain", J. Neurosci. Res., May 1, 1997, vol. 48, issue 3, pp. 249-258, Abstract Only.
Meunier, et al., "Isolation and structure of the endogenous agonist of opioid receptor-like ORL1 receptor", Nature, vol. 377, Oct. 12, 1995, pp. 532-535, Abstract Only.
Igwe, et al., "Specific Binding of Substance P Amino-terminal Heptapeptide [SP( I-7)] to Mouse Brain and Spinal Cord Membranes", J. Neurosci., vol. 10, issue 11, Nov. 1990, pp. 3653-3663.
Bartlett, et al., "Selective and rapid uptake of adeno-associated virus type 2 in brain", Hum. Gene. Ther., vol. 9, issue 8, May 20, 1998, pp. 1181-1186, Abstract only.
Tenenbaum et al., "Evaluation of Risks Related to the Use of Adeno-Associated Virus-Based Vectors" 2003, Curr. Gene Ther., vol. 3, pp. 545-565.

(Continued)

Primary Examiner — John D Ulm
(74) Attorney, Agent, or Firm — Hovey Williams LLP

(57) ABSTRACT

The invention relates to novel peptides, polypeptides or proteins which bind specifically to brain cells and/or to the spinal cord. The peptides, polypeptides, or proteins can be components of a viral capsid and can be used to lead a recombinant viral vector selectively to the brain and/or spinal cord after systemic administration to a subject and to ensure tissue-specific expression of one or more transgenes there. The invention also relates to a recombinant viral vector, preferably an AAV vector, which comprises a capsid containing at least one of the claimed peptides, polypeptides, or proteins and which comprises at least one transgene packaged in the capsid. Said viral vector can be used, in particular for the therapeutic treatment of a disease or disorder of the brain and/or spinal cord. The invention further relates to cells and pharmaceutical compositions that comprise the viral vector according to the invention.

44 Claims, 5 Drawing Sheets

Specification includes a Sequence Listing.

(56) References Cited

OTHER PUBLICATIONS

Work et al., "Vascular Bed-Targeted in Vivo Gene Delivery Using Tropism-Modified Adeno-associated Viruses", Apr. 2006, Mol. Ther., vol. 4, pp. 683-693.
Shi et al., "Insertional Mutagenesis at Positions 520 and 584 of Adeno-Associated Virus Type 2 (AAV2) Capsid Gene and Generation of AAV2 Vectors with Eliminated Heparin-Binding Ability and Introduced Novel Tropism", Mar. 2006, Hum. Gene Ther., vol. 17, pp. 353-361.
Michelfelder et al.,"Successful Expansion but Not Complete Restriction of Tropism of Adeno-Associated Virus by In Vivo Biopanning of Random Virus Display Peptide Libraries", 2009, PLOS One, vol. 4, issue 4, 13 pages.
Kaplitt et al.,"Safety and tolerability of gene therapy with an adeno-associated virus (AAV) borne GAD gene for Parkinson's disease: an open label, phase I trial", Jun. 23, 2007, Lancet, vol. 369, issue 9579, pp. 2097-2105.
Gray et al., "Directed Evolution of a Novel Adeno-associated Virus (AAV) Vector That Crosses the Seizure-compromised Blood-Brain Barrier (BBB)", Mar. 2010, Mol. Ther., vol. 18, issue 3, pp. 570-578.
Shevtsova et al., "Promoters and serotypes: targeting of adeno-associated virus vectors for gene transfer in the rat central nervous system in vitro and in vivo", 2005, Exp. Physiol., vol. 90, issue 1, pp. 53-59.
Gray et al., "Optimizing Promoters for Recombinant Adeno-Associated Virus-Mediated Gene Expression in the Peripheral and Central Nervous System Using Self-Complementary Vectors", Sep. 2011, Hum. Gene Ther., vol. 22, issue 9, pp. 1143-1153.
Aebischer et al., "Intrathecal delivery of CNTF using encapsulated genetically modified xenogenic cells in amyotrophic lateral sclerosis patients", Jun. 1996, Nat. Med., vol. 2, issue 6, pp. 696-699.
McCown et al., "Differential and persistent expression patterns of CNS gene transfer by an adeno-associated virus (AAV) vector", 1996, Brain Res., vol. 713, issue 1-2, pp. 99-107.
During et al., "In vivo expression of therapeutic human genes for dopamine production in the caudates of MPTP-treated monkeys using an AAV vector", 1998, Gene Ther., vol. 5, issue 6, pp. 820-827.
Kalburgi et al., "Recent Gene Therapy Advancements for Neurological Diseases", Feb. 2013, Discov. Med., vol. 15, issue 81, pp. 111-119.
Alonso et al., "Focal Delivery of AAV2/1-transgenes Into the Rat Brain by Localized Ultrasound-induced BBB Opening", 2013, Mol. Ther. Nucleic Acids, vol. 2, 7 pages.
Shi et al., "RGD Inclusion in VP3 Provides Adeno-Associated Virus Type 2 (AAV2)-Based Vectors with a Heparan Sulfate-Independent Cell Entry Mechanism", Apr. 2003, Mol. Ther., vol. 7, issue 4, pp. 515-525.
Loiler et al., "Targeting recombinant adeno-associated virus vectors to enhance gene transfer to pancreatic islets and liver", Feb. 2003, Gene Ther., vol. 10, pp. 1551-1558.
Rabinowitz et al., "Insertional Mutagenesis of AAV2 Capsis and the Production of Recombinant Virus", 1999, Virology, vol. 265, pp. 274-285.
Wu et al., "Mutational Analysis of the Adeno-Associated Virus Type 2 (AAV2) Capsid Gene and Construction of AAV2 Vectors with Altered Tropism", Sep. 2000, J. Virol, vol. 74, issue 18, pp. 8635-8647.
Shi et al., "Insertional Mutagenesis of the Adeno-Associated Virus Type 2 (AAV2) Capsid Gene and Generation of AAV2 Vectors Targeted to Alternative Cell-Surface Receptors", Sep. 20, 2001, Hum. Gene Ther., vol. 12, pp. 1697-1711.
Warrington et al., "Adeno-Associated Virus Type 2 VP2 Capsid Protein Is Nonessential and Can Tolerate Large Peptide Insertions at Its N Terminus", Jun. 2004, J. Virol., vol. 78, issue 12, pp. 6595-6609.
Girod et al., "Genetic capsid modifications allow efficient re-targeting of adeno-associated virus type 2", Sep. 1999, Nat. Med., vol. 5, issue 9, pp. 1052-1056.
Grifman et al., "Incorporation of Tumor-Targeting Peptides into Recombinant Adeno-associated Virus Capsids", Jun. 2001, Mol. Ther., vol. 3, issue 6, pp. 964-975.
Opie et al., "Identification of Amino Acid Residues in the Capsid Proteins of Adeno-Associated Virus Type 2 That Contribute to Heparan Sulfate Proteoglycan Binding", Jun. 2003, J. Virol., vol. 77, issue 12, pp. 6995-7006.
Kern et al., "Identification of a Heparin-Binding Motif on Adeno-Associated Virus Type 2 Capsids", Oct. 2003, J. Virol., vol. 77, issue 20, pp. 11072-11081.
Ruthledge et al., "Infectious Clones and Vectors Derived from Adeno-Associated Virus (AAV) Serotypes Other Than AAV Type 2", Jan. 1998, J. Virol., vol. 72, issue 1, pp. 309-319.
Muller et al., "Random peptide libraries displayed on adeno-associated virus to select for targeted gene therapy vectors", Sep. 2003, Nat. Biotechnol., vol. 21, issue 9, pp. 1040-1046.
Waterkamp et al., "Isolation of targeted AAV2 vectors from novel virus display libraries", 2006, J. Gene Med., vol. 8, pp. 1307-1319.
Xiao et al., "Production of High-Titer Recombinant Adeno-Associated Virus Vectors in the Absence of Helper Adenovirus", Mar. 1998, J. of Virology, vol. 72, issue 3, pp. 2224-2232.
Zolotukhin et al., "Recombinant adeno-associated virus purification using novel methods improves infectious titer and yield", 1999, Gene Ther., vol. 6, pp. 973-985.
McCarty et al., "Self-complementary recombinant adeno-associated virus (scAAV) vectors promote efficient transduction independently of DNA synthesis", 2001, Gene Ther., vol. 8, pp. 1248-1254.
Michelfelder et al., "Vectors selected from adeno-associated viral display peptide libraries for leukemia cell-targeted cytotoxic gene therapy", 2007, Exp. Hematol., vol. 35, pp. 1766-1776.
Rohr et al., "Quantitative real-time PCR for titration of infectious recombinant AAV-2 particles", 2005, J. Virol. Methods, vol. 127, pp. 40-45.
Urabe et al., "Insect Cells as a Factory to Produce Adeno-Associated Virus Type 2 Vectors", Nov. 1, 2002, Hum. Gene Ther., vol. 13, pp. 1935-1943.
Kohlbrenner et al., "Successful Production of Pseudotyped rAAV Vectors Using a Modified Baculovirus Expression System", Dec. 2005, Mol. Ther., vol. 12, issue 6, pp. 1217-1225.
Chen, "Intron Splicing-mediated Expression of AAV Rep and Cap Genes and Production of AAV Vectors in Insect Cells", May 2008, Mol. Ther., vol. 16, issue 5, pp. 924-930.
Office Action in related German Patent Application Serial No. 102014207498.3, dated Sep. 8, 2014 (English translation attached).
International Search Report and Written Opinion in corresponding PCT Application Serial No. PCT/EP2015/058123, 26 pages, dated Nov. 12, 2015 (English translation attached).
XP_002487045, "Talaromyces Stipitatus ATCC 10500", Oct. 1, 2007.
Barst et al., Diagnosis and Differential Assessment of Pulmonary Arterial Hypertension, 2004 Journal of the American College of Cardiology, vol. 43, No. 12 pp. 40-47 (8 pages).
McLaughlin et al., ACCF/AHA 2009 Expert Consensus Document on Pulmonary Hypertension, A Report of the American College of Cardiology Foundation Task Force on Expert Consensus Documents and the American Heart Association, Circulation, 2009, 119: 2250-2294 (47 pages).
Stenmark et al., Animal models of pulmonary arterial hypertension: the hope for etiological discovery and pharmacological cure, Am J Physiol Lung Cell Mol Physiol, Sep. 11, 2009, 297: 1013-1032 (20 pages).
Friedman et al., Obesity and Pulmonary Hypertension: A Review of PathophysiologicMechanisms, 2012 Journal of Obesity, vol. 2012: 505274 (9 pages).
Chin et al., The right ventricle in pulmonary hypertension, Coronary Artery Disease, 2005, vol. 16 No. 1: 13-18 (6 pages).
Hemnes et al., Right heart function and haemodynamics in pulmonary hypertension, International Journal of Clinical Practice (Suppl. 160), Jul. 2008,11-19 (9 pages).
Humbert et al., Update in Pulmonary Hypertension 2008, Am J Respir Crit Care Med, Jan. 26, 2009, vol. 179, pp. 650-656 (7 pages).

(56) References Cited

OTHER PUBLICATIONS

Simonneau et al., Updated Clinical Classification of Pulmonary Hypertension, Journal of the American College of Cardiology, 2009, vol. 54, No. 1, Suppl S: 43-54 (12 pages).
Humbert et al., Pulmonary Arterial Hypertension in France, Am J Respir Crit Care Med, Feb. 2, 2006, vol. 173 pp. 1023-1030 (8 pages).
Russell et al., Infectious Clones and Vectors Derived from Adeno-Associated Virus (AAV) Serotypes Other Than AAV Type 2, Journal of Virology, Jan. 1998, vol. 72, No. 1: 309-319 (11 pages).
Database UniProt [Online] Sep. 13, 2005 (Sep. 13, 2005), "RecName: Full=Sugar fermentation stimulation protein homolog;", EBI accession No. UNIPROT:Q47W67 Database accession No. Q47W67 (1 page).
Michelfelder et al: Peptide Ligands Incorporated into the Threefold Spike Capsid Domain to Re-Direct Gene Transduction of AAV8 and AAV9 In Vivo, PLOS ONE, vol. 6, No. 8, Aug. 5, 2011 (Aug. 5, 2011), pp. e23101.
Ying et al: Heart-targeted adeno-associated viral vectors selected by in vivo biopanning of a random viral display peptide library, Gene Therapy, vol. 17, No. 8, Apr. 15, 2010 (Apr. 15, 2010), pp. 980-990 (11 pages).
International Search Report in PCT/EP2014/066892, dated Nov. 5, 2014, English Translation (3 pages), corresponding to co-pending national stage case U.S. Appl. No. 14/911,197.
Written Opinion in PCT/EP2014/066892, dated Nov. 5, 2014, English Translation (6 pages), corresponding to co-pending national stage case U.S. Appl. No. 14/911,197.
Internet—Search dated Feb. 19, 2014 Major coat protein VP1 [Adeno-associated virus—21 Accession No. YP-680426 (1 page).
Internet—Search dated Feb. 19, 2014 Sequence comparison SEQ ID No. 9 from co-pending U.S. Appl. No. 14/911,197 and YP-680426 (3 pages).
Office action from co-pending U.S. Appl. No. 14/911,197, dated Nov. 24, 2017 (17 pages).
Korbelin, et al., "Pulmonary Targeting of Adeno-associated Viral Vectors by Next-generation Sequencing-guided Screening of Random Capsid Displayed Peptide Libraries" American Socity of Gene & Cell Therapy, Jun. 2016, vol. 24, issue 6, pp. 1050-1061.
Office action from co-pending U.S. Appl. No. 14/911,197, dated Jul. 19, 2018 (16 pages).

* cited by examiner

| Round 1 | Round 2 | Round 3 | Round 4 | Round 5 |
|---|---|---|---|---|
| GWQPQVQ SEQ ID NO:22 | NRTADTG SEQ ID NO:32 | (NNVRTSE)[2] SEQ ID NO:39 | NMARQAD SEQ ID NO:40 | NMARQAD SEQ ID NO:40 |
| GSDKGES SEQ ID NO:23 | NSGYGYT SEQ ID NO:33 | (SDGLTWS)[6] SEQ ID NO:4 | NRGTEWD SEQ ID NO:1 | (SDGLTWS)[8] SEQ ID NO:41 |
| GTDGGEN SEQ ID NO:24 | (NNVRTSE)[4] SEQ ID NO:34 | DDGVSWK SEQ ID NO:3 | (SDGLTWS)[6] SEQ ID NO:4 | DDGVSWK SEQ ID NO:42 |
| NAERGEG SEQ ID NO:25 | NESRRLE SEQ ID NO:35 | | SDGLAWV SEQ ID NO:5 | |
| NNATRDW SEQ ID NO:26 | GGGKRRE SEQ ID NO:36 | | ADGVQWT SEQ ID NO:2 | |
| NSAARIE SEQ ID NO:27 | EGDIRWV SEQ ID NO:37 | | | |
| NSAARWE SEQ ID NO:28 | SNYSRVM SEQ ID NO:38 | | | |
| KDAWERE SEQ ID NO:29 | | | | |
| KKQQWDQ SEQ ID NO:30 | | | | |
| AHGAEQA SEQ ID NO:31 | | | | |

Fig. 2

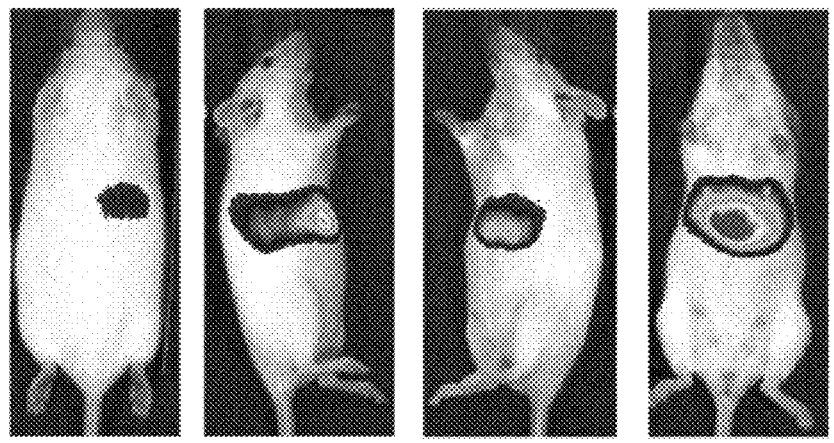
A  wild-type rAAV2
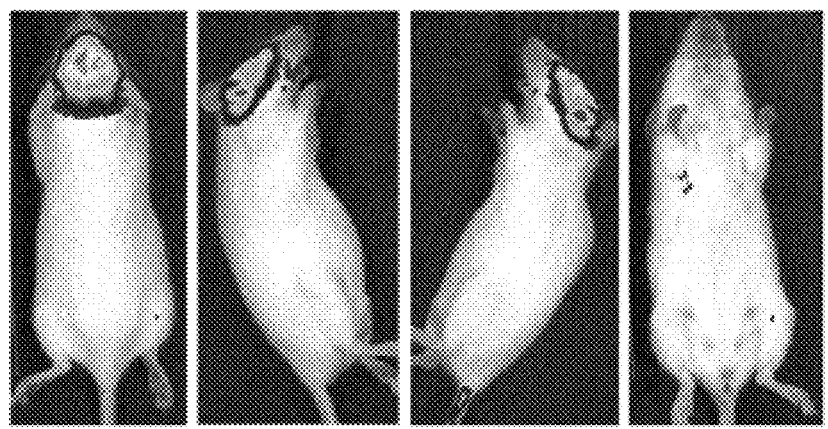
B  rAAV2-NRGTEWD
Fig. 3

```
                          SEQUENCE LISTING

<160> NUMBER OF SEQ ID NOS: 42

<210> SEQ ID NO 1
<211> LENGTH: 7
<212> TYPE: PRT
<213> ORGANISM: Artificial Sequence
<220> FEATURE:
<223> OTHER INFORMATION: brain specific peptide

<400> SEQUENCE: 1

Asn Arg Gly Thr Glu Trp Asp
1               5

<210> SEQ ID NO 2
<211> LENGTH: 7
<212> TYPE: PRT
<213> ORGANISM: Artificial Sequence
<220> FEATURE:
<223> OTHER INFORMATION: brain specific peptide

<400> SEQUENCE: 2

Ala Asp Gly Val Gln Trp Thr
1               5

<210> SEQ ID NO 3
<211> LENGTH: 7
<212> TYPE: PRT
<213> ORGANISM: Artificial Sequence
<220> FEATURE:
<223> OTHER INFORMATION: brain specific peptide

<400> SEQUENCE: 3

Asp Asp Gly Val Ser Trp Lys
1               5

<210> SEQ ID NO 4
<211> LENGTH: 42
<212> TYPE: PRT
<213> ORGANISM: Artificial Sequence
<220> FEATURE:
<223> OTHER INFORMATION: brain specific peptide

<400> SEQUENCE: 4

Ser Asp Gly Leu Thr Trp Ser Ser Asp Gly Leu Thr Trp Ser Ser Asp
1               5                   10                  15

Gly Leu Thr Trp Ser Ser Asp Gly Leu Thr Trp Ser Ser Asp Gly Leu
                20                  25                  30

Thr Trp Ser Ser Asp Gly Leu Thr Trp Ser
                35                  40
```

<210> SEQ ID NO 5
<211> LENGTH: 7
<212> TYPE: PRT
<213> ORGANISM: Artificial Sequence
<220> FEATURE:
<223> OTHER INFORMATION: brain specific peptide

<400> SEQUENCE: 5

```
Ser Asp Gly Leu Ala Trp Val
1               5
```

<210> SEQ ID NO 6
<211> LENGTH: 7
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 6

```
Xaa Asp Gly Xaa Xaa Trp Xaa
1               5
```

<210> SEQ ID NO 7
<211> LENGTH: 735
<212> TYPE: PRT
<213> ORGANISM: adeno-associated virus 2

<400> SEQUENCE: 7

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175
```

```
Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
```

```
                595                 600                 605
Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 8
<211> LENGTH: 598
<212> TYPE: PRT
<213> ORGANISM: adeno-associated virus 2

<400> SEQUENCE: 8

Met Ala Pro Gly Lys Lys Arg Pro Val Glu His Ser Pro Val Glu Pro
1               5                   10                  15

Asp Ser Ser Ser Gly Thr Gly Lys Ala Gly Gln Gln Pro Ala Arg Lys
            20                  25                  30

Arg Leu Asn Phe Gly Gln Thr Gly Asp Ala Asp Ser Val Pro Asp Pro
        35                  40                  45

Gln Pro Leu Gly Gln Pro Pro Ala Ala Pro Ser Gly Leu Gly Thr Asn
    50                  55                  60

Thr Met Ala Thr Gly Ser Gly Ala Pro Met Ala Asp Asn Asn Glu Gly
65                  70                  75                  80

Ala Asp Gly Val Gly Asn Ser Ser Gly Asn Trp His Cys Asp Ser Thr
                85                  90                  95

Trp Met Gly Asp Arg Val Ile Thr Thr Ser Thr Arg Thr Trp Ala Leu
            100                 105                 110

Pro Thr Tyr Asn Asn His Leu Tyr Lys Gln Ile Ser Ser Gln Ser Gly
        115                 120                 125

Ala Ser Asn Asp Asn His Tyr Phe Gly Tyr Ser Thr Pro Trp Gly Tyr
    130                 135                 140

Phe Asp Phe Asn Arg Phe His Cys His Phe Ser Pro Arg Asp Trp Gln
145                 150                 155                 160

Arg Leu Ile Asn Asn Asn Trp Gly Phe Arg Pro Lys Arg Leu Asn Phe
                165                 170                 175

Lys Leu Phe Asn Ile Gln Val Lys Glu Val Thr Gln Asn Asp Gly Thr
            180                 185                 190

Thr Thr Ile Ala Asn Asn Leu Thr Ser Thr Val Gln Val Phe Thr Asp
        195                 200                 205

Ser Glu Tyr Gln Leu Pro Tyr Val Leu Gly Ser Ala His Gln Gly Cys
    210                 215                 220

Leu Pro Pro Phe Pro Ala Asp Val Phe Met Val Pro Gln Tyr Gly Tyr
225                 230                 235                 240
```

```
Leu Thr Leu Asn Asn Gly Ser Gln Ala Val Gly Arg Ser Ser Phe Tyr
            245                 250                 255

Cys Leu Glu Tyr Phe Pro Ser Gln Met Leu Arg Thr Gly Asn Asn Phe
        260                 265                 270

Thr Phe Ser Tyr Thr Phe Glu Asp Val Pro Phe His Ser Ser Tyr Ala
    275                 280                 285

His Ser Gln Ser Leu Asp Arg Leu Met Asn Pro Leu Ile Asp Gln Tyr
290                 295                 300

Leu Tyr Tyr Leu Ser Arg Thr Asn Thr Pro Ser Gly Thr Thr Thr Gln
305                 310                 315                 320

Ser Arg Leu Gln Phe Ser Gln Ala Gly Ala Ser Asp Ile Arg Asp Gln
                325                 330                 335

Ser Arg Asn Trp Leu Pro Gly Pro Cys Tyr Arg Gln Gln Arg Val Ser
            340                 345                 350

Lys Thr Ser Ala Asp Asn Asn Asn Ser Glu Tyr Ser Trp Thr Gly Ala
        355                 360                 365

Thr Lys Tyr His Leu Asn Gly Arg Asp Ser Leu Val Asn Pro Gly Pro
    370                 375                 380

Ala Met Ala Ser His Lys Asp Asp Glu Glu Lys Phe Phe Pro Gln Ser
385                 390                 395                 400

Gly Val Leu Ile Phe Gly Lys Gln Gly Ser Glu Lys Thr Asn Val Asp
                405                 410                 415

Ile Glu Lys Val Met Ile Thr Asp Glu Glu Ile Arg Thr Thr Asn
            420                 425                 430

Pro Val Ala Thr Glu Gln Tyr Gly Ser Val Ser Thr Asn Leu Gln Arg
        435                 440                 445

Gly Asn Arg Gln Ala Ala Thr Ala Asp Val Asn Thr Gln Gly Val Leu
    450                 455                 460

Pro Gly Met Val Trp Gln Asp Arg Asp Val Tyr Leu Gln Gly Pro Ile
465                 470                 475                 480

Trp Ala Lys Ile Pro His Thr Asp Gly His Phe His Pro Ser Pro Leu
                485                 490                 495

Met Gly Gly Phe Gly Leu Lys His Pro Pro Pro Gln Ile Leu Ile Lys
            500                 505                 510

Asn Thr Pro Val Pro Ala Asn Pro Ser Thr Thr Phe Ser Ala Ala Lys
        515                 520                 525

Phe Ala Ser Phe Ile Thr Gln Tyr Ser Thr Gly Gln Val Ser Val Glu
    530                 535                 540

Ile Glu Trp Glu Leu Gln Lys Glu Asn Ser Lys Arg Trp Asn Pro Glu
545                 550                 555                 560

Ile Gln Tyr Thr Ser Asn Tyr Asn Lys Ser Val Asn Val Asp Phe Thr
                565                 570                 575

Val Asp Thr Asn Gly Val Tyr Ser Glu Pro Arg Pro Ile Gly Thr Arg
            580                 585                 590

Tyr Leu Thr Arg Asn Leu
        595

<210> SEQ ID NO 9
<211> LENGTH: 533
<212> TYPE: PRT
<213> ORGANISM: adeno-associated virus 2

<400> SEQUENCE: 9

Met Ala Thr Gly Ser Gly Ala Pro Met Ala Asp Asn Asn Glu Gly Ala
1               5                   10                  15
```

```
Asp Gly Val Gly Asn Ser Ser Gly Asn Trp His Cys Asp Ser Thr Trp
            20                  25                  30

Met Gly Asp Arg Val Ile Thr Thr Ser Thr Arg Thr Trp Ala Leu Pro
        35                  40                  45

Thr Tyr Asn Asn His Leu Tyr Lys Gln Ile Ser Ser Gln Ser Gly Ala
50                  55                  60

Ser Asn Asp Asn His Tyr Phe Gly Tyr Ser Thr Pro Trp Gly Tyr Phe
65                  70                  75                  80

Asp Phe Asn Arg Phe His Cys His Phe Ser Pro Arg Asp Trp Gln Arg
                85                  90                  95

Leu Ile Asn Asn Asn Trp Gly Phe Arg Pro Lys Arg Leu Asn Phe Lys
            100                 105                 110

Leu Phe Asn Ile Gln Val Lys Glu Val Thr Gln Asn Asp Gly Thr Thr
        115                 120                 125

Thr Ile Ala Asn Asn Leu Thr Ser Thr Val Gln Val Phe Thr Asp Ser
130                 135                 140

Glu Tyr Gln Leu Pro Tyr Val Leu Gly Ser Ala His Gln Gly Cys Leu
145                 150                 155                 160

Pro Pro Phe Pro Ala Asp Val Phe Met Val Pro Gln Tyr Gly Tyr Leu
            165                 170                 175

Thr Leu Asn Asn Gly Ser Gln Ala Val Gly Arg Ser Ser Phe Tyr Cys
        180                 185                 190

Leu Glu Tyr Phe Pro Ser Gln Met Leu Arg Thr Gly Asn Asn Phe Thr
        195                 200                 205

Phe Ser Tyr Thr Phe Glu Asp Val Pro Phe His Ser Ser Tyr Ala His
        210                 215                 220

Ser Gln Ser Leu Asp Arg Leu Met Asn Pro Leu Ile Asp Gln Tyr Leu
225                 230                 235                 240

Tyr Tyr Leu Ser Arg Thr Asn Thr Pro Ser Gly Thr Thr Thr Gln Ser
            245                 250                 255

Arg Leu Gln Phe Ser Gln Ala Gly Ala Ser Asp Ile Arg Asp Gln Ser
            260                 265                 270

Arg Asn Trp Leu Pro Gly Pro Cys Tyr Arg Gln Gln Arg Val Ser Lys
        275                 280                 285

Thr Ser Ala Asp Asn Asn Asn Ser Glu Tyr Ser Trp Thr Gly Ala Thr
        290                 295                 300

Lys Tyr His Leu Asn Gly Arg Asp Ser Leu Val Asn Pro Gly Pro Ala
305                 310                 315                 320

Met Ala Ser His Lys Asp Asp Glu Glu Lys Phe Phe Pro Gln Ser Gly
            325                 330                 335

Val Leu Ile Phe Gly Lys Gln Gly Ser Glu Lys Thr Asn Val Asp Ile
        340                 345                 350

Glu Lys Val Met Ile Thr Asp Glu Glu Ile Arg Thr Thr Asn Pro
        355                 360                 365

Val Ala Thr Glu Gln Tyr Gly Ser Val Ser Thr Asn Leu Gln Arg Gly
        370                 375                 380

Asn Arg Gln Ala Ala Thr Ala Asp Val Asn Thr Gln Gly Val Leu Pro
385                 390                 395                 400

Gly Met Val Trp Gln Asp Arg Asp Val Tyr Leu Gln Gly Pro Ile Trp
            405                 410                 415

Ala Lys Ile Pro His Thr Asp Gly His Phe His Pro Ser Pro Leu Met
        420                 425                 430
```

```
Gly Gly Phe Gly Leu Lys His Pro Pro Gln Ile Leu Ile Lys Asn
            435                 440                 445

Thr Pro Val Pro Ala Asn Pro Ser Thr Thr Phe Ser Ala Ala Lys Phe
450                 455                 460

Ala Ser Phe Ile Thr Gln Tyr Ser Thr Gly Gln Val Ser Val Glu Ile
465                 470                 475                 480

Glu Trp Glu Leu Gln Lys Glu Asn Ser Lys Arg Trp Asn Pro Glu Ile
                485                 490                 495

Gln Tyr Thr Ser Asn Tyr Asn Lys Ser Val Asn Val Asp Phe Thr Val
                500                 505                 510

Asp Thr Asn Gly Val Tyr Ser Glu Pro Arg Pro Ile Gly Thr Arg Tyr
            515                 520                 525

Leu Thr Arg Asn Leu
    530

<210> SEQ ID NO 10
<211> LENGTH: 744
<212> TYPE: PRT
<213> ORGANISM: adeno-associated virus 2

<400> SEQUENCE: 10

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270
```

```
Phe Gly Tyr Ser Thr Pro Trp Gly Tyr Phe Asp Phe Asn Arg Phe His
            275                 280                 285
Cys His Phe Ser Pro Arg Asp Trp Gln Arg Leu Ile Asn Asn Asn Trp
    290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
            355                 360                 365
Val Phe Met Val Pro Gln Tyr Gly Tyr Leu Thr Leu Asn Asn Gly Ser
    370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Ser Arg Thr
    435                 440                 445
Asn Thr Pro Ser Gly Thr Thr Thr Gln Ser Arg Leu Gln Phe Ser Gln
    450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
                485                 490                 495
Asn Ser Glu Tyr Ser Trp Thr Gly Ala Thr Lys Tyr His Leu Asn Gly
            500                 505                 510
Arg Asp Ser Leu Val Asn Pro Gly Pro Ala Met Ala Ser His Lys Asp
            515                 520                 525
Asp Glu Glu Lys Phe Phe Pro Gln Ser Gly Val Leu Ile Phe Gly Lys
    530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Arg Gly Asn Arg Gly
            580                 585                 590
Thr Glu Trp Asp Ala Gln Ala Ala Thr Ala Asp Val Asn Thr Gln Gly
    595                 600                 605
Val Leu Pro Gly Met Val Trp Gln Asp Arg Asp Val Tyr Leu Gln Gly
    610                 615                 620
Pro Ile Trp Ala Lys Ile Pro His Thr Asp Gly His Phe His Pro Ser
625                 630                 635                 640
Pro Leu Met Gly Gly Phe Gly Leu Lys His Pro Pro Pro Gln Ile Leu
                645                 650                 655
Ile Lys Asn Thr Pro Val Pro Ala Asn Pro Ser Thr Thr Phe Ser Ala
            660                 665                 670
Ala Lys Phe Ala Ser Phe Ile Thr Gln Tyr Ser Thr Gly Gln Val Ser
            675                 680                 685
```

```
Val Glu Ile Glu Trp Glu Leu Gln Lys Glu Asn Ser Lys Arg Trp Asn
    690                 695                 700
Pro Glu Ile Gln Tyr Thr Ser Asn Tyr Asn Lys Ser Val Asn Val Asp
705                 710                 715                 720
Phe Thr Val Asp Thr Asn Gly Val Tyr Ser Glu Pro Arg Pro Ile Gly
                725                 730                 735
Thr Arg Tyr Leu Thr Arg Asn Leu
            740
```

<210> SEQ ID NO 11
<211> LENGTH: 8359
<212> TYPE: DNA
<213> ORGANISM: adeno-associated virus 2

<400> SEQUENCE: 11

```
catcatcaat aatataccct attttggatt gaagccaata tgataatgag ggggtggagt      60
ttgtgacgtg gcgcggggcg tgggaacggg gcgggtgacg tagtagctct agaggtcctg     120
tattagaggt cacgtgagtg ttttgcgaca ttttgcgaca ccatgtggtc acgctgggta     180
tttaagcccg agtgagcacg cagggtctcc attttgaagc gggaggtttg aacgcgcagc     240
cgccatgccg ggttttacg agattgtgat taaggtcccc agcgaccttg acgagcatct     300
gcccggcatt tctgacagct ttgtgaactg ggtggccgag aaggaatggg agttgccgcc     360
agattctgac atggatctga atctgattga gcaggcaccc ctgaccgtgg ccgagaagct     420
gcagcgcgac tttctgacgg aatggcgccg tgtgagtaag caccggaggc cctttttctt     480
tgtgcaattt gagaagggag agagctactt ccacatgcac gtgctcgtgg aaaccaccgg     540
ggtgaaatcc atggttttgg acgtttcct gagtcagatt cgcgaaaaac tgattcagag     600
aatttaccgc gggatcgagc cgactttgcc aaactggttc gcggtcacaa agaccagaaa     660
tggcgccgga ggcgggaaca aggtggtgga tgagtgctac atccccaatt acttgctccc     720
caaaacccag cctgagctcc agtgggcgtg gactaatatg gaacagtatt taagcgcctg     780
tttgaatctc acggagcgta acggttggt ggcgcagcat ctgacgcacg tgtcgcagac     840
gcaggagcag aacaaagaga tcagaatcc aattctgat gccggtga tcagatcaaa     900
aacttcagcc aggtacatgg agctggtcgg gtggctcgtg acaagggga ttacctcgga     960
gaagcagtgg atccaggagg accaggcctc atacatctcc ttcaatgcgg cctccaactc    1020
gcggtcccaa atcaaggctg ccttggacaa tgcgggaaag attatgagcc tgactaaaac    1080
cgcccccgac tacctggtgg ccagcagcc cgtggaggac atttccagca atcggattta    1140
taaattttg gaactaaacg ggtacgatcc ccaatatgcg gcttccgtct ttctgggatg    1200
ggccacgaaa aagttcggca agaggaacac catctggctg tttgggcctg caactaccgg    1260
gaagaccaac atcgcggagg ccatagccca cactgtgccc ttctacgggt gcgtaaactg    1320
gaccaatgag aactttcccct tcaacgactg tgtcgacaag atggtgatct ggtgggagga    1380
ggggaagatg accgccaagg tcgtggagtc ggccaaagcc attctcggag gaagcaaggt    1440
gcgcgtggac cagaaatgca gtcctcggc ccagatagac ccgactcccg tgatcgtcac    1500
ctccaacacc aacatgtgcg ccgtgattga cgggaactca acgaccttcg aacaccagca    1560
gccgttgcaa gaccggatgt tcaaatttga actcacccgc gtctggatc atgactttgg    1620
gaaggtcacc aagcaggaag tcaaagactt tttccggtgg gcaaaggatc acgtggttga    1680
ggtggagcat gaattctacg tcaaaaaggg tggagccaag aaaagacccg ccccagtga    1740
cgcagatata agtgagccca acggggtgcg cgagtcagtt gcgcagccat cgacgtcaga    1800
```

```
cgcggaagct tcgatcaact acgcagacag gtaccaaaac aaatgttctc gtcacgtggg   1860
catgaatctg atgctgtttc cctgcagaca atgcgagaga atgaatcaga attcaaatat   1920
ctgcttcact cacggacaga aagactgttt agagtgcttt cccgtgtcag aatctcaacc   1980
cgtttctgtc gtcaaaaagg cgtatcgaaa actgtgctac attcatcata tcatgggaaa   2040
ggtgccagac gcttgcactg cctgcgatct ggtcaatgtg gatttggatg actgcatctt   2100
tgaacaataa atgatttaaa tcaggtatgg ctgccgatgg ttatcttcca gattggctcg   2160
aggacactct ctctgaagga ataagacagt ggtggaagct caaacctggc ccaccaccac   2220
caaagcccgc agagcggcat aaggacgaca gcagggtct tgtgcttcct gggtacaagt    2280
acctcggacc cttcaacgga ctcgacaagg gagagccggt caacgaggca gacgccgcgg   2340
ccctcgagca cgacaaagcc tacgaccggc agctcgacag cggagacaac ccgtacctca   2400
agtacaacca cgccgacgcg gagtttcagg agcgccttaa agaagatacg tcttttgggg   2460
gcaacctcgg acgagcagtc ttccaggcga aaaagagggt tcttgaacct ctgggcctgg   2520
ttgaggaacc tgttaagacg gctccgggaa aaagaggcc ggtagagcac tctcctgtgg    2580
agccagactc ctcctcggga accggaaagg cgggccagca gcctgcaaga aaaagattga   2640
attttggtca gactggagac gcagactcag tacctgaccc ccagcctctc ggacagccac   2700
cagcagcccc ctctggtctg gaactaata cgatggctac aggcagtggc gcaccaatgg    2760
cagacaataa cgagggcgcc gacggagtgg gtaattcctc gggaaattgg cattgcgatt   2820
ccacatggat gggcgacaga gtcatcacca ccagcacccg aacctgggcc ctgcccacct   2880
acaacaacca cctctacaaa caaatttcca gccaatcagg agcctcgaac gacaatcact   2940
actttggcta cagcacccct tgggggtatt ttgacttcaa cagattccac tgccacttt    3000 caccacgtga ctggcaaaga ctcatcaaca caactgggg attccgaccc aagagactca    3060
acttcaagct ctttaacatt caagtcaaag aggtcacgca gaatgacggt acgacgacga   3120
ttgccaataa ccttaccagc acggttcagg tgtttactga ctcggagtac cagctcccgt   3180
acgtcctcgg ctcggcgcat caaggatgcc tcccgccgtt cccagcagac gtcttcatgg   3240
tgccacagta tggataccctc accctgaaca acggagtca ggcagtagga cgctcttcat    3300
tttactgcct ggagtacttt ccttctcaga tgctgcgtac cggaaacaac tttaccttca   3360
gctacacttt tgaggacgtt cctttccaca gcagctacgc tcacagccag agtctggacc   3420
gtctcatgaa tcctctcatc gaccagtacc tgtattactt gagcagaaca aacactccaa   3480
gtggaaccac cacgcagtca aggcttcagt tttctcaggc cggagcgagt gacattcggg   3540
accagtctag gaactggctt cctggaccct gttaccgcca gcagcgagta tcaaagacat   3600
ctgcggataa caacaacagt gaatactcgt ggactggagc taccaagtac cacctcaatg   3660
gcagagactc tctggtgaat ccgggcccgg ccatggcaag ccacaaggac gatgaagaaa   3720
agttttttcc tcagagcggg gttctcatct ttgggaagca aggctcagag aaaacaaatg   3780
tggacattga aaaggtcatg attacagacg aagaggaaat caggacaacc aatcccgtgg   3840
ctacggagca gtatggttct gtatctacca acctccagag aggccagaga ggcaatcggg   3900
ggactgagtg ggatgcccag gcggccaccg cagatgtcaa cacacaaggc gttcttccag   3960
gcatggtctg gcaggacaga gatgtgtacc ttcagggcc catctgggca aagattccac   4020
acacggacga acattttcac ccctctcccc tcatgggtgg attcggactt aaacacccct   4080
ctccacagat tctcatcaag aacaccccgg tacctgcgaa tccttcgacc accttcagtg   4140
```

```
cggcaaagtt tgcttccttc atcacacagt actccacggg acaggtcagc gtggagatcg    4200
agtgggagct gcagaaggaa aacagcaaac gctggaatcc cgaaattcag tacacttcca    4260
actacaacaa gtctgttaat gtggacttta ctgtggacac taatggcgtg tattcagagc    4320
ctcgccccat tggcaccaga tacctgactc gtaatctgta attgcttgtt aatcaataaa    4380
ccgtttaatt cgtttcagtt gaactttggt ctctgcgtat ttctttctta tctagtttcc    4440
atgctctaga ggtcctgtat tagaggtcac gtgagtgttt tgcgacattt tgcgacacca    4500
tgtggtcacg ctgggtattt aagcccgagt gagcacgcag ggtctccatt ttgaagcggg    4560
aggtttgaac gcgcagccac cacggcgggg ttttacgaga ttgtgattaa ggtccccagc    4620
gaccttgacg agcatctgcc cggcatttct gacagctttg tgaactgggt ggccgagaag    4680
gaatgggagt tgccgccaga ttctgacatg gatctgaatc tgattgagca ggcacccctg    4740
accgtggccg agaagctgca tcgctggcgt aatagcgaag aggcccgcac cgatcgccct    4800
tcccaacagt tgcgcagcct gaatggcgaa tggcgattcc gttgcaatgg ctggcggtaa    4860
tattgttctg gatattacca gcaaggccga tagtttgagt tcttctactc aggcaagtga    4920
tgttattact aatcaaagaa gtattgcgac aacggttaat ttgcgtgatg gacagactct    4980
tttactcggt ggcctcactg attataaaaa cacttctcag gattctggcg taccgttcct    5040
gtctaaaatc cctttaatcg gcctcctgtt tagctcccgc tctgattcta acgaggaaag    5100
cacgttatac gtgctcgtca aagcaaccat agtacgcgcc ctgtagcggc gcattaagcg    5160
cggcgggtgt ggtggttacg cgcagcgtga ccgctacact tgccagcgcc ctagcgcccg    5220
ctcctttcgc tttcttccct tcctttctcg ccacgttcgc cggctttccc cgtcaagctc    5280
taaatcgggg gctcccttta gggttccgat ttagtgcttt acggcacctc gaccccaaaa    5340
aacttgatta gggtgatggt tcacgtagtg gccatcgcc ctgatagacg ttttttcgcc    5400
ctttgacgtt ggagtccacg ttctttaata gtggactctt gttccaaact ggaacaacac    5460
tcaaccctat ctcggtctat tcttttgatt tataagggat tttgccgatt tcggcctatt    5520
ggttaaaaaa tgagctgatt taacaaaaat ttaacgcgaa ttttaacaaa atattaacgt    5580
ttacaattta aatatttgct tatacaatct tcctgttttt ggggcttttc tgattatcaa    5640
ccggggtaca tatgattgac atgctagttt tacgattacc gttcatcgat tctcttgttt    5700
gctccagact ctcaggcaat gacctgatag cctttgtaga cctctcaa aaatagctac    5760 cctctccggc atgaatttat cagctagaac ggttgaatat catattgatg gtgatttgac    5820
tgtctccggc ctttctcacc cgtttgaatc tttacctaca cattactcag gcattgcatt    5880
taaaatatat gagggttcta aaaattttta tccttgcgtt gaaataaagg cttctcccgc    5940
aaaagtatta cagggtcata atgttttttgg tacaaccgat ttagctttat gctctgaggc    6000
tttattgctt aattttgcta attctttgcc ttgcctgtat gatttattgg atgttggaat    6060
tcctgatgcg gtattttctc cttacgcatc tgtgcggtat ttcacaccgc atatggtgca    6120
ctctcagtac aatctgctct gatgccgcat agttaagcca gccccgacac ccgccaacac    6180
ccgctgacgc gccctgacgg gcttgtctgc tcccggcatc cgcttacaga caagctgtga    6240
ccgtctccgg gagctgcatg tgtcagaggt tttcaccgtc atcaccgaaa cgcgcgagac    6300
gaaagggcct cgtgatacgc ctatttttat aggttaatgt catgataata atggtttctt    6360
agacgtcagg tggcacttt cggggaaatg tgcgcggaac ccctatttgt ttattttct    6420 aaatacattc aaatatgtat ccgctcatga gacaataacc ctgataaatg cttcaataat    6480
attgaaaaag gaagagtatg agtattcaac atttccgtgt cgcccttatt cccttttttg    6540
```

```
cggcattttg ccttcctgtt tttgctcacc cagaaacgct ggtgaaagta aaagatgctg    6600
aagatcagtt gggtgcacga gtgggttaca tcgaactgga tctcaacagc ggtaagatcc    6660
ttgagagttt tcgccccgaa gaacgttttc caatgatgag cacttttaaa gttctgctat    6720
gtggcgcggt attatcccgt attgacgccg gcaagagca actcggtcgc cgcatacact    6780
attctcagaa tgacttggtt gagtactcac cagtcacaga aaagcatctt acggatggca    6840
tgacagtaag agaattatgc agtgctgcca taaccatgag tgataacact gcggccaact    6900
tacttctgac aacgatcgga ggaccgaagg agctaaccgc ttttttgcac aacatggggg    6960
atcatgtaac tcgccttgat cgttgggaac cggagctgaa tgaagccata ccaaacgacg    7020
agcgtgacac cacgatgcct gtagcaatgg caacaacgtt gcgcaaacta ttaactggcg    7080
aactacttac tctagcttcc cggcaacaat taatagactg gatggaggcg gataaagttg    7140
caggaccact tctgcgctcg gcccttccgg ctggctggtt tattgctgat aaatctggag    7200
ccggtgagcg tgggtctcgc ggtatcattg cagcactggg gccagatggt aagccctccc    7260
gtatcgtagt tatctacacg acggggagtc aggcaactat ggatgaacga atagacaga    7320 tcgctgagat aggtgcctca ctgattaagc attggtaact gtcagaccaa gtttactcat    7380
atatacttta gattgattta aaacttcatt tttaatttaa aaggatctag gtgaagatcc    7440
tttttgataa tctcatgacc aaaatccctt aacgtgagtt ttcgttccac tgagcgtcag    7500
accccgtaga aaagatcaaa ggatcttctt gagatccttt ttttctgcgc gtaatctgct    7560
gcttgcaaac aaaaaaacca ccgctaccag cggtggtttg tttgccggat caagagctac    7620
caactctttt tccgaaggta actggcttca gcagagcgca gataccaaat actgtccttc    7680
tagtgtagcc gtagttaggc caccacttca agaactctgt agcaccgcct acatacctcg    7740
ctctgctaat cctgttacca gtggctgctg ccagtggcga taagtcgtgt cttaccgggt    7800
tggactcaag acgatagtta ccggataagg cgcagcggtc gggctgaacg gggggttcgt    7860
gcacacagcc cagcttggag cgaacgacct acaccgaact gagatacta cagcgtgagc    7920 tatgagaaag cgccacgctt cccgaaggga gaaaggcgga caggtatccg gtaagcggca    7980
gggtcggaac aggagagcgc acgagggagc ttccaggggg aaacgcctgg tatctttata    8040
gtcctgtcgg gtttcgccac ctctgacttg agcgtcgatt tttgtgatgc tcgtcagggg    8100
ggcggagcct atgaaaaac gccagcaacg cggccttttt acggttcctg gccttttgct    8160
ggccttttgc tcacatgttc tttcctgcgt tatcccctga ttctgtggat aaccgtatta    8220
ccgcctttga gtgagctgat accgctcgcc gcagccgaac gaccgagcgc agcgagtcag    8280
tgagcgagga agcggaagag cgcccaatac gcaaaccgcc tctccccgcg cgttggccga    8340
ttcattaatg cagaattcc                                                 8359
```

<210> SEQ ID NO 12
<211> LENGTH: 56
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: (18)..(38)
<223> OTHER INFORMATION: n is a, c, g, or t

<400> SEQUENCE: 12

```
cagtcggcca gagaggcnnn nnnnnnnnn nnnnnnnngc ccaggcggct gacgag          56
```

```
<210> SEQ ID NO 13
<211> LENGTH: 16
<212> TYPE: DNA
<213> ORGANISM: Artificial Sequence
<220> FEATURE:
<223> OTHER INFORMATION: PCR Primer

<400> SEQUENCE: 13
ctcgtcagcc gcctgg                                                         16

<210> SEQ ID NO 14
<211> LENGTH: 26
<212> TYPE: DNA
<213> ORGANISM: Artificial Sequence
<220> FEATURE:
<223> OTHER INFORMATION: PCR Primer

<400> SEQUENCE: 14
gcagtatggt tctgtatcta ccaacc                                              26

<210> SEQ ID NO 15
<211> LENGTH: 22
<212> TYPE: DNA
<213> ORGANISM: Artificial Sequence
<220> FEATURE:
<223> OTHER INFORMATION: PCR Primer

<400> SEQUENCE: 15
gcctggaaga acgccttgtg tg                                                  22

<210> SEQ ID NO 16
<211> LENGTH: 22
<212> TYPE: DNA
<213> ORGANISM: Artificial Sequence
<220> FEATURE:
<223> OTHER INFORMATION: PCR Primer

<400> SEQUENCE: 16
atggcaagcc acaaggacga tg                                                  22

<210> SEQ ID NO 17
<211> LENGTH: 22
<212> TYPE: DNA
<213> ORGANISM: Artificial Sequence
<220> FEATURE:
<223> OTHER INFORMATION: PCR Primer

<400> SEQUENCE: 17
cgtggagtac tgtgtgatga ag                                                  22

<210> SEQ ID NO 18
<211> LENGTH: 23
<212> TYPE: DNA
<213> ORGANISM: Artificial Sequence
<220> FEATURE:
<223> OTHER INFORMATION: PCR Primer

<400> SEQUENCE: 18
ggttctcatc tttgggaagc aag                                                 23

<210> SEQ ID NO 19
<211> LENGTH: 21
<212> TYPE: DNA
<213> ORGANISM: Artificial Sequence
<220> FEATURE:
<223> OTHER INFORMATION: PCR Primer
```

<400> SEQUENCE: 19
tgatgagaat ctgtggagga g                                       21

<210> SEQ ID NO 20
<211> LENGTH: 19
<212> TYPE: DNA
<213> ORGANISM: Artificial Sequence
<220> FEATURE:
<223> OTHER INFORMATION: PCR Primer

<400> SEQUENCE: 20
ggcggagttg ttacgacat                                          19

<210> SEQ ID NO 21
<211> LENGTH: 20
<212> TYPE: DNA
<213> ORGANISM: Artificial Sequence
<220> FEATURE:
<223> OTHER INFORMATION: PCR Primer

<400> SEQUENCE: 21
gggactttcc ctacttggca                                         20

<210> SEQ ID NO 22
<211> LENGTH: 7
<212> TYPE: PRT
<213> ORGANISM: Artificial Sequence
<220> FEATURE:
<223> OTHER INFORMATION: brain specific peptide

<400> SEQUENCE: 22

Gly Trp Gln Pro Gln Val Gln
1               5

<210> SEQ ID NO 23
<211> LENGTH: 7
<212> TYPE: PRT
<213> ORGANISM: Artificial Sequence
<220> FEATURE:
<223> OTHER INFORMATION: brain specific peptide

<400> SEQUENCE: 23

Gly Ser Asp Lys Gly Glu Ser
1               5

<210> SEQ ID NO 24
<211> LENGTH: 7
<212> TYPE: PRT
<213> ORGANISM: Artificial Sequence
<220> FEATURE:
<223> OTHER INFORMATION: brain specific peptide

<400> SEQUENCE: 24

Gly Thr Asp Gly Gly Glu Asn
1               5

<210> SEQ ID NO 25
<211> LENGTH: 7
<212> TYPE: PRT
<213> ORGANISM: Artificial Sequence
<220> FEATURE:
<223> OTHER INFORMATION: brain specific peptide

<400> SEQUENCE: 25

Asn Ala Glu Arg Gly Glu Gly 1               5

<210> SEQ ID NO 26
<211> LENGTH: 7
<212> TYPE: PRT
<213> ORGANISM: Artificial Sequence
<220> FEATURE:
<223> OTHER INFORMATION: brain specific peptide

<400> SEQUENCE: 26

Asn Asn Ala Thr Arg Asp Trp
1               5

<210> SEQ ID NO 27
<211> LENGTH: 7
<212> TYPE: PRT
<213> ORGANISM: Artificial Sequence
<220> FEATURE:
<223> OTHER INFORMATION: brain specific peptide

<400> SEQUENCE: 27

Asn Ser Ala Ala Arg Ile Glu
1               5

<210> SEQ ID NO 28
<211> LENGTH: 7
<212> TYPE: PRT
<213> ORGANISM: Artificial Sequence
<220> FEATURE:
<223> OTHER INFORMATION: brain specific peptide

<400> SEQUENCE: 28

Asn Ser Ala Ala Arg Trp Glu
1               5

<210> SEQ ID NO 29
<211> LENGTH: 7
<212> TYPE: PRT
<213> ORGANISM: Artificial Sequence
<220> FEATURE:
<223> OTHER INFORMATION: brain specific peptide

<400> SEQUENCE: 29

Lys Asp Ala Trp Glu Arg Glu
1               5

<210> SEQ ID NO 30
<211> LENGTH: 7
<212> TYPE: PRT
<213> ORGANISM: Artificial Sequence
<220> FEATURE:
<223> OTHER INFORMATION: brain specific peptide

<400> SEQUENCE: 30

Lys Lys Gln Gln Trp Asp Gln
1               5

<210> SEQ ID NO 31
<211> LENGTH: 7
<212> TYPE: PRT
<213> ORGANISM: Artificial Sequence
<220> FEATURE:
<223> OTHER INFORMATION: brain specific peptide

<400> SEQUENCE: 31

Ala His Gly Ala Glu Gln Ala
1               5

```
<210> SEQ ID NO 32
<211> LENGTH: 7
<212> TYPE: PRT
<213> ORGANISM: Artificial Sequence
<220> FEATURE:
<223> OTHER INFORMATION: brain specific peptide

<400> SEQUENCE: 32

Asn Arg Thr Ala Asp Thr Gly
1               5

<210> SEQ ID NO 33
<211> LENGTH: 7
<212> TYPE: PRT
<213> ORGANISM: Artificial Sequence
<220> FEATURE:
<223> OTHER INFORMATION: brain specific peptide

<400> SEQUENCE: 33

Asn Ser Gly Tyr Gly Tyr Thr
1               5

<210> SEQ ID NO 34
<211> LENGTH: 28
<212> TYPE: PRT
<213> ORGANISM: Artificial Sequence
<220> FEATURE:
<223> OTHER INFORMATION: brain specific peptide

<400> SEQUENCE: 34

Asn Asn Val Arg Thr Ser Glu Asn Asn Val Arg Thr Ser Glu Asn Asn
1               5                   10                  15

Val Arg Thr Ser Glu Asn Asn Val Arg Thr Ser Glu
            20                  25

<210> SEQ ID NO 35
<211> LENGTH: 7
<212> TYPE: PRT
<213> ORGANISM: Artificial Sequence
<220> FEATURE:
<223> OTHER INFORMATION: brain specific peptide

<400> SEQUENCE: 35

Asn Glu Ser Arg Arg Leu Glu
1               5

<210> SEQ ID NO 36
<211> LENGTH: 7
<212> TYPE: PRT
<213> ORGANISM: Artificial Sequence
<220> FEATURE:
<223> OTHER INFORMATION: brain specific peptide

<400> SEQUENCE: 36

Gly Gly Gly Lys Arg Arg Glu
1               5

<210> SEQ ID NO 37
<211> LENGTH: 7
<212> TYPE: PRT
<213> ORGANISM: Artificial Sequence
<220> FEATURE:
<223> OTHER INFORMATION: brain specific peptide

<400> SEQUENCE: 37
```

Glu Gly Asp Ile Arg Trp Val
1               5

<210> SEQ ID NO 38
<211> LENGTH: 7
<212> TYPE: PRT
<213> ORGANISM: Artificial Sequence
<220> FEATURE:
<223> OTHER INFORMATION: brain specific peptide

<400> SEQUENCE: 38

Ser Asn Tyr Ser Arg Val Met
1               5

<210> SEQ ID NO 39
<211> LENGTH: 14
<212> TYPE: PRT
<213> ORGANISM: Artificial Sequence
<220> FEATURE:
<223> OTHER INFORMATION: brain specific peptide

<400> SEQUENCE: 39

Asn Asn Val Arg Thr Ser Glu Asn Asn Val Arg Thr Ser Glu
1               5                   10

<210> SEQ ID NO 40
<211> LENGTH: 7
<212> TYPE: PRT
<213> ORGANISM: Artificial Sequence
<220> FEATURE:
<223> OTHER INFORMATION: brain specific peptide

<400> SEQUENCE: 40

Asn Met Ala Arg Gln Ala Asp
1               5

<210> SEQ ID NO 41
<211> LENGTH: 56
<212> TYPE: PRT
<213> ORGANISM: Artificial Sequence
<220> FEATURE:
<223> OTHER INFORMATION: brain specific peptide

<400> SEQUENCE: 41

Ser Asp Gly Leu Thr Trp Ser Ser Asp Gly Leu Thr Trp Ser Ser Asp
1               5                   10                  15
Gly Leu Thr Trp Ser Ser Asp Gly Leu Thr Trp Ser Ser Asp Gly Leu
            20                  25                  30
Thr Trp Ser Ser Asp Gly Leu Thr Trp Ser Ser Asp Gly Leu Thr Trp
        35                  40                  45
Ser Ser Asp Gly Leu Thr Trp Ser
    50                  55

<210> SEQ ID NO 42
<211> LENGTH: 7
<212> TYPE: PRT
<213> ORGANISM: Artificial Sequence
<220> FEATURE:
<223> OTHER INFORMATION: brain specific peptide

<400> SEQUENCE: 42

Asp Asp Gly Val Ser Trp Lys
1               5

VIRAL VECTOR FOR THE TARGETED TRANSFER OF GENES IN THE BRAIN AND SPINAL CORD

RELATED APPLICATIONS

This application is the National Stage of International patent application No. PCT/EP2015/058123, filed Apr. 15, 2015, which is hereby incorporated by reference in its entirety, and which claims priority to German Patent application No. 102014207498.3, filed Apr. 17, 2014.

SEQUENCE LISTING

The sequences listed in the accompanying Sequence Listing are presented in accordance with 37 C.F.R. 1.822. The Sequence Listing is submitted as an ASCII computer readable text file, which is incorporated by reference herein.

The invention relates to novel peptides, polypeptides or proteins which specifically bind to cells of the brain and/or the spinal cord. The peptides, polypeptides or proteins can be part of a viral capsid, and they can be used for guiding a recombinant viral vector selectively to the brain and/or spinal cord after systemic administration to a subject, where it provides for a tissue-specific expression of one or more transgenes. The invention therefore also relates to a recombinant viral vector, preferably an AAV vector, comprising a capsid containing at least one of the peptides, polypeptides or proteins of the invention and at least one transgene which is packaged within the capsid. The viral vector is particularly suitable for the therapeutic treatment of a disease or functional disorder of the brain and/or the spinal cord. The invention further relates to cells and pharmaceutical compositions comprising the viral vector of the invention.

BACKGROUND OF THE INVENTION

The gene therapeutic treatment by use of viral vectors is a promising treatment option for diseases that do not respond or do not sufficiently respond to conventional treatment. This approach is based on the introduction of therapeutic genes into the organism to be treated using viruses which have been modified to include the sequence of the respective gene in their genome. Viral vectors which have been used for gene therapy in gene therapeutic approaches are based on retroviruses, lentiviruses, adenoviruses and adeno-associated viruses.

Adeno-associated viruses (AAV) are promising candidates for use in clinical practice because they are considered as relatively safe. AAV vectors are capable of introducing a transgene into a tissue and expressing same stably and efficiently. At the same time, these vectors do not possess any known pathogenic mechanism [1]. The AAV vectors of serotype 2 (AAV2) are of particular importance for clinical use, and these vectors have been examined particularly well. After introduction by AAV vectors, the transgenes can be present within the transfected cell in different forms, for example as episomal, single-stranded or double-stranded DNA. Concatemeric forms of DNA were also found in transduced cells.

The genome of AAV2 is a linear, single-stranded DNA molecule of approximately 4700 nucleotides in length, and it comprises inverted terminal repeats (ITRs) at both ends. The genome further comprises two large open reading frames which are referred to as replication region (rep) and capsid region (cap). The replication region encodes proteins which are required in connection with virus replication. In contrast, the capsid region encodes the structural proteins VP1, VP2 and VP3 which make up the icosahedral capsid of the virus.

As most of the vectors which can be used in gene therapy and which are known in the state of the art, wild-type AAV vectors, e.g. the disclosed AAV2 vectors, do not possess sufficient specificity for a specific tissue but instead infect a wide variety of cell types. Upon systemic administration of these wild-type vectors, the target tissue is insufficiently transduced, and severe immune reactions have to be expected in the treated patient due to the undesired transduction of other tissues. Progress has been made with the development of viral vectors having an increased specificity for particular organs by using peptide ligands that are capable of guiding the vectors to specific organs [2-3]. It could be shown that specific peptide ligands provide for a "homing" to different organs such as the brain.

Reference [4] describes a method that allows for the screening of capsids of AAV2 with modified tropism in randomized peptide libraries. From these libraries, vectors can be isolated that specifically transduce a desired cell type in vitro. However, it has been found that capsids selected in this way are often unsuitable for being used in vivo since the required specificity is missing in an animal model [5].

From the clinical perspective, the brain is an extremely relevant organ, since it is the starting point of a variety of neurological diseases. Considerable efforts have been made to make this organ accessible for gene therapeutic interventions [6-12]. However, the blood brain barrier, which is composed of endothelial cells, pericytes and astrocytes and which seals the brain off from circulating particles, toxins and signal compounds, represents a barrier that cannot be passed by normal vector systems. Since suitable vector systems that transduce the brain with sufficient efficiency after intravenous application are not available so far, present gene therapy vectors are normally injected directly into the brain [13] which is associated with a higher risk for the patient. The possibility of making the blood brain barrier permeable for a short time, e.g. by ultrasound [14] or by chemical agents [7] is also regarded as very risky.

Accordingly, there is a high demand for agents, which are capable of modulating the tropism of viral vectors, thereby providing for a sufficient cell or tissue specificity which renders possible a targeted transport of a viral vector to tissues of the brain or spinal cord. Such vectors can provide for the specific expression of therapeutic genes in these tissues, thereby effectively treating diseases and/or functional conditions of the brain and the spinal cord.

The present invention provides viral vectors for the targeted gene transfer into the brain and spinal cord. The viral vectors of the present invention express on their capsid surface so far unknown amino acid sequences that are specifically recognized in vivo by receptors on the neurons of the brain and the endothelial cells of the blood vessels of the brain and spinal cord. In this way, the viral vectors of the present invention, after systemic administration to a subject, specifically transduce the tissues in the brain and spinal cord.

The viral vectors of the present invention further enable a strong and long persisting expression of a transgene in the neurons of the brain and in the endothelial cells of the blood vessels of the brain and spinal cord. Therefore, the vectors are particularly suitable for the gene therapeutic treatment of defined diseases or conditions of the brain and spinal cord. It has been furthermore found that the AAV vectors produce

DESCRIPTION OF THE INVENTION

In the present invention, various sequences that are specific for the central nervous system, i.e. for the brain and spinal cord, were identified by selection in a randomized AAV2 heptamer peptide library. A heptamer having particular specificity for the brain was peptide NRGTEWD (SEQ ID NO:1). Based on this sequence, the recombinant viral vector rAAV2-NRGTEWD (SEQ ID NO:1) was produced which expresses the peptide sequence NRGTEWD (SEQ ID NO:1) as a partial sequence of the capsid protein VP1. Subsequently, vector rAAV2-NRGTEWD (SEQ ID NO:1) was administered intravenously to mice and a clear specificity of the vector for the central nervous system could be observed both in vitro and in vivo. Both neurons of the brain and endothelial cells of the blood vessels of the brain and the spinal cords were transfected by the vector. The specificity was confirmed by staining with CD31 as described in the present examples.

A further group of peptides, which also showed specificity for the brain and spinal cord, encompassed peptides ADGVQWT (SEQ ID NO:2), DDGVSWK (SEQ ID NO:3), SDGLTWS (SEQ ID NO:4) and SDGLAWV (SEQ ID NO:5). These peptides contained the general motif XDGXXWX (SEQ ID NO: 6).

The present invention therefore provides different peptide sequences which are specific for the brain and spinal cord and which are particularly suitable for guiding therapeutic agents, such as viral vectors, to the brain or spinal cord of a subject to be treated, respectively.

In a first aspect, the present invention therefore relates to a peptide, polypeptide or protein which specifically binds to cells of the brain and/or spinal cord, wherein the peptide, polypeptide or protein comprises the amino acid sequence of SEQ ID NO:1 or a variant thereof, wherein the variant differs from the amino acid sequence of SEQ ID NO:1 by modification of a maximum of one amino acid. The peptide, polypeptide or protein of the present invention preferably binds to endothelial cells and/or neurons of the brain or spinal cord.

In a second aspect, the present invention relates to a peptide, polypeptide or protein, which specifically binds to cells of the brain and/or spinal cord, wherein the peptide, polypeptide or protein comprises the general amino acid sequence of SEQ ID NO:6. In a particularly preferred embodiment, the peptide, polypeptide or protein comprises one of the sequences of ADGVQWT (SEQ ID NO:2), DDGVSWK (SEQ ID NO:3), SDGLTWS (SEQ ID NO:4) or SDGLAWV (SEQ ID NO:5) or a variant thereof, wherein the variant differs from the respective amino acid sequence of SEQ ID NO:2-5 by modification of a maximum of one amino acid. The peptide, polypeptide or protein of the present invention preferably binds to endothelial cells and/or neurons of the brain or spinal cord.

In the context of the present disclosure, the term "peptide" refers to a linkage of 2-10 amino acids which are connected to each other by a peptide bond. The term "polypeptide" refers to a linkage of 11-100 amino acids that are connected to each other by a peptide bond. Polypeptides with more than 100 amino acids are referred to herein as a "protein."

In a particularly preferred embodiment according to the invention, the peptide sequence of SEQ ID NO:1 or a variant thereof or SEQ ID NO:2-6 or a variant thereof, which are specific for the brain and spinal cord, is a part of a capsid protein of a virus. This means that the sequence, which is specific for the brain and spinal cord, is present as part of a capsid protein of the virus. To produce such capsid proteins, a corresponding nucleotide sequence which codes for the peptide is cloned into the region of the virus genome which codes for a capsid protein of the virus. If the sequence, which is specific for the brain and the spinal cord, respectively, is expressed as part of a capsid protein, it can be presented in many copies across the surface of the viral vector.

The capsid protein is preferably one which is derived from an adeno-associated virus (AAV). The AAV can be any of the serotypes described in the prior art, wherein the capsid protein is preferably derived from an AAV of one of the serotypes 2, 4, 6, 8 and 9. A capsid protein of an AAV of serotype 2 is particularly preferred.

The capsid of the AAV wild-type is made up of the capsid proteins VP1, VP2 and VP3, which are encoded by the overlapping cap region. All three proteins have the same C-terminal region. The capsid of AAV comprises about 60 copies of the proteins VP1, VP2 and VP3, expressed in a ratio of 1:1:8. If a nucleotide sequence coding for one of the peptides, which is specific for the brain and the spinal cord, respectively, and which is described herein is cloned at the C-terminus into the reading frame of VP1 (i.e., in the region that is identical in all three proteins), it can be expected that theoretically 60 of the specific peptides can be found on the capsid surface.

If an AAV vector in the context of the present invention is modified, the nucleotide sequence coding for the peptide which is specific for the brain is then cloned into the cap region at the 3' end of the genome. The sequence encoding the peptide being specific for the brain and spinal cord, respectively, can be cloned into the genomic sequence of one of the capsid proteins VP1, VP2 or VP3. The capsid proteins of AAV2 are illustrated by way of example in SEQ ID NO:7 (VP1), SEQ ID NO:8 (VP2), and SEC ID NO:9 (VP3).

In one particularly preferred embodiment according to the invention, the sequence encoding the peptide, which is specific for the brain and spinal cord, respectively, is cloned into the reading frame of a VP1 gene, preferably in the VP1 gene of AAV2 shown in SEQ ID NO:7. It should be noted in this case that the insertion of the cloned sequence does not lead to any change of the reading frame, nor to a premature termination of translation. The methods required for the above will be readily apparent to a person skilled in the art.

In all three capsid proteins of AVV, sites have been identified at which peptide sequences can be inserted for the homing function [15-20]. Among other things, the arginine which occurs in the VP1 of AAV2 at position 588 (R588) has specifically been proposed for the insertion of a peptide ligand [21-22]. This amino acid position of the viral capsid is apparently involved in the binding of AAV2 to its natural receptor. It has been suggested that R588 is one of four arginine residues which mediates the binding of AAV2 to its natural receptor [23-24]. A modification in this region of the capsid weakens the natural tropism of AAV2, or eliminates it completely.

Accordingly, it is particularly preferred according to the invention that the peptide sequence of SEQ ID NO:1 or a variant thereof or of SEC ID NO:2-6 or a variant thereof is present in inserted form in the region of the amino acids 550-600 of the VP1 protein of AAV2, in particular of the VP1 protein of SEQ ID NO:7. Even more preferably, the peptide sequence is present in inserted form in the region of amino acids 560-600, J570-600, 560-590, 570-590 of the VP1 protein.

Thus, the peptide sequence of SEQ ID NO:1 or a variant thereof or SEQ ID NO:2-6 or a variant thereof can adjoin, by way of example, directly behind one of the following amino acids of the VP1 protein, particularly the protein of SEQ ID NO:7: 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599 or 600.

It is particularly preferred that the amino acid sequence of SEQ ID NO:1 or a variant thereof or SEQ ID NO: 2-6 or a variant thereof follows the amino acid 588 of the VP1 protein of SEQ ID NO:7, as shown in the examples. It is possible in this case that one or more, and particularly up to 5 (i.e., 1, 2, 3, 4 or 5) amino acids which are the result of the cloning are situated between the arginine residue at position 588 and the first amino acid of the peptide of the invention or the variant thereof. Likewise, one or more, and particularly up to 5 (i.e., 1, 2, 3, 4, or 5) amino acids can be situated behind the last amino acid of the peptide of the invention or the variant thereof.

The sites and regions in the amino acid sequence of the capsid protein indicated above for VP1 apply analogously to the capsid proteins VP2 and VP3 of AAV2. Because the three capsid proteins VP1, VP2 and VP3 of AAV2 differ only by the length of the N-terminal sequence and accordingly have an identical C-terminus, a person skilled in the art will have no problem making a sequence comparison to identify the sites indicated above, for the insertion of the peptide ligands, in the amino acid sequences of VP1 and VP2. As such, the amino acid 588 in VP1 corresponds to position VP1 of VP2 (SEQ ID NO: 8) and position R386 of VP3 (SEQ ID NO:9), respectively.

SEQ ID NO:10 shows an example of the sequence of the VP1 protein of AAV2 after introduction of the peptide sequence of SEQ ID NO:1. Due to the cloning, the capsid protein has two additional amino acids which do not occur in the native sequence of the VP1 protein of AAV2. As such, the peptide sequence of SEQ ID NO:1 is flanked at its N-terminus by a glycine in position 589, and at its C-terminus by an alanine in position 597. In addition, the asparagine at position 587 of the native sequence is replaced with a glutamine.

In one particular embodiment, the present invention therefore also relates to a capsid protein which comprises or consists of:

(a) the amino acid sequence of SEQ ID NO:10;
(b) an amino acid sequence which is at least 80%, and preferably 90, 95 or 99%, identical to the amino acid sequence of SEQ ID NO:10 and furthermore (i) comprises the amino acid sequence of SEQ ID NO:1 or (ii) an amino acid sequence, which differs from. the amino acid. sequence of SEQ ID NO:1 by modification. of one amino acid; or
(c) a fragment of one of the amino acid sequences defined in (a) or (b).

In a further aspect, the invention is directed to a viral capsid, which comprises a peptide, polypeptide or protein which specifically binds to cells of the brain or spinal cord, respectively, and comprises the amino acid sequence of SEQ ID NO:1 or a variant thereof or SEQ ID NO:2-6 or a variant thereof.

Furthermore, the present invention also provides a nucleic acid encoding a peptide, polypeptide or protein as described above. A nucleic acid which encodes a capsid protein which comprises a peptide, polypeptide or protein according to the invention as described above, is likewise provided. Preferably, the nucleic acid coding for the capsid protein comprises the nucleotide sequence of SEQ ID NO:11 or a nucleotide sequence derived from the same with at least 80% sequence identity. A plasmid comprising such a nucleic acid is also provided.

In yet another aspect, the invention relates to a recombinant —i.e., produced by means of genetic engineering techniques—viral vector, having a capsid and at least one transgene packaged therein, wherein the capsid comprises at least one capsid protein having the amino acid sequence of SEQ ID NO:1 or a variant thereof or SEQ ID NO:2-6 or a variant thereof. The recombinant viral vector can be a recombinant AAV vector—for example, of serotype 2, 4, 6, 8, 9. AAV vectors of serotype 2 are particularly preferred.

The different AAV serotypes differ mainly by their natural tropism. As such, wild-type AAV2 binds more readily to alveolar cells, while AAV5, AAV6 and AAV9 mainly infect epithelial cells. A person skilled in the art can take advantage of these natural differences in the specificity of the cells to further enhance the specificity mediated by the peptides according to the invention for certain cells or tissues. At the nucleic acid level, the various AAV serotypes are highly homologous. For example, serotypes AAV1, AAV2, AAV3 and AAV6 are 82% identical on the nucleic acid level [25].

The capsid of the viral vectors according to the invention comprises one or more transgenes. A gene which has been introduced by genetic engineering into the genome of the vector is termed a transgene. The transgene (or transgenes) can be DNA or RNA. Preferably, it is single-stranded DNA (ssDNA) or double-stranded DNA (dsDNA), such as genomic DNA or cDNA. Preferably, the transgene which is to be transported with the aid of the recombinant viral vector according to the invention is a human gene. Suitable transgenes include, for example, therapeutic genes to replace a dysfunctional gene in patients. They can also be genes which are not expressed in the corresponding target tissue, or are only expressed to an insufficient extent. In one preferred embodiment, the transgene which is expressed from the viral vector according to the invention is a.

The vectors of the present invention can be used, amongst others, for the treatment of Multiple Sclerosis (MS). In this case, the transgene can be, e.g. a gene which encodes a membrane protein or a tight junction protein, such as for claudin and occludin. Preferably the transgene is a gene from the family of claudins, e.g. the gene encoding claudin 1. The overexpression of one of such genes could be helpful for "sealing" the blood brain barrier that is damaged by the disease.

In addition, a gene can be used for the treatment of MS which encodes a chemokine antagonist. For example, a negative-dominant mutant of the chemokine CCL2 (aka MCP1) can be expressed which is referred to as "CCL2-7ND". CCL2 provides for the attraction of immune cells to the site of inflammation which in the case of MS results in the inflammatory degradation of the myelin sheaths of neurons. In contrast, the dominant-negative variant "CCL2-7ND" forms dimers and blocks the receptor CCL2, thereby interfering with the signal cascade such that the immune cells are no longer attracted by the neurons.

For the treatment of Alzheimer's Disease, e.g. the gene encoding neuraminidase 1 (NEU1), neprilysine or cholesterol 24 hydroxylase can be overexpressed which leads to the degradation of amyloid β plaques and therefore can contribute to an amelioration of the state of disease.

Parkinson's disease can be treated by vector-mediated overexpression of e.g. the neurotrophic factors of glia cells (GDNF), the aromatic L-amino acid decarboxylase, the tyrosine hydroxylase or the GTP cyclohydrolase 1, wherein a positive influence on the dopaminergic system can be expected. A treatment of the spinal muscle atrophy can be achieved, e.g. by expression of the protein SMN (survival of motor neuron).

For the therapy of a lysosomal storage disease, the expression of glucuronidase, e.g. β-glucuronidase, as a transgene by use of the vectors of the present invention would be promising. In a further embodiment, the transgene encodes a radio-protective protein such as a radioprotective enzyme. A major limitation of radiotherapy in the treatment of cancer is the radiation-induced damage to the normal tissue, which often makes a reduction in radiation dose, an interruption of the treatment regimen, or even a complete abandonment of this form of therapy necessary. The brain is a particularly radiosensitive organ, which is why primary tumors there often can only be treated to a limited extent with radiotherapy, and diffuse tumor growth usually cannot be treated at all with radiotherapy. With the help of the vectors of the present invention, the healthy tissue surrounding the malignant tissue can be protected by targeted expression of radioprotective proteins. In one preferred embodiment, the transgene which is introduced into the healthy brain tissue is a manganese superoxide dismutase (MnSOD) which catalyzes the conversion of superoxide anions—one of the critical factors in radiation-induced toxicity—to hydrogen peroxide. A further embodiment proposed here involves the kinase domain of the Ataxia telangiectasia mutant (ATM) gene, which contributes to the repair of DNA damage caused by radiation. In a further preferred embodiment, both genes are introduced by means of the presently described vectors into the patient undergoing treatment.

The viral vectors of the present invention are particularly suitable for use in a method of therapeutic treatment of diseases of the brain and/or spinal cord. Diseases of the brain and spinal cord, respectively, in the sense of the present invention comprise genetically caused leukodystrophies, such as adrenoleukodystrophy, Cananvan disease, Krabbe disease, metachromatic leukodystrophy, Pelizaeus-Merzbacher disease and Alexander disease; neurodegenerative diseases such as amyotrophic lateral sclerosis, Alzheimer's disease, Parkinson's disease, Huntington's disease and Pick's disease; chronic-inflammatory diseases of the central nervous system such as Multiple Sclerosis and Guillain-Barré syndrome and lysosomal storage diseases such as ceroid lipofuscinosis and Fabry disease. In a particularly preferred embodiment, the viral vectors of the present invention are for the therapeutic treatment of neurodegenerative diseases such as Alzheimer's disease, Parkinson's disease or Huntington's disease.

In yet another embodiment, the transgene encodes an antitumor agent, such as a tumor suppressor protein, or an immunomodulator, such as a cytokine (e.g. interleukin 1 to 4, gamma-interferon, p53), which is intended to be transported selectively to a brain tumor or a tumor of the spinal cord of the patient.

The vectors can also be used to transport antisense-RNA, ribozymes, or the like into cells or tissues of the brain or spinal cord. Furthermore, vectors according to the invention can also comprise transgenes encoding secretory proteins that are intended for being released to the microvasculature of the brain or spinal cord. Such secretory proteins can be effective, e.g. as anti-inflammatory agents.

As used herein, the term "subject" indicates any human or animal organism that can be infected by AAV vectors. Preferably, the subject being treated is a mammal such as a human, a primate, a mouse or a rat. In one preferred embodiment, the subject to be treated is a human. After transfection into the subject, the vector brings about a site-specific expression of the transgene in the cells of the brain or spinal cord.

The transgene can be present in the viral vector in the form of an expression cassette, which in addition to the sequence of the transgene to be expressed comprises further elements necessary for expression, such as a suitable promoter which controls the expression of the transgene after infection of the appropriate cells. Suitable promoters include, in addition to the AAV promoters, e.g. the cytomegalovirus (CMV) promoter or the chicken beta actin/cytomegalovirus hybrid promoter (CAG), an endothelial cell-specific promoter such as the VE-cadherin promoter, as well as steroid promoters and metallothionein promoters. In one particularly preferred embodiment, the promoter used in the vectors according to the invention is a CAG promoter. In one particularly preferred embodiment, the transgene according to the invention comprises a brain-specific promoter which is functionally linked to the transgene to be expressed. In this way, the specificity of the vectors according to the invention for the brain can be further increased. As used herein, a brain-specific promoter is a promoter whose activity in brain tissue is at least 2-fold, 5-fold, 10-fold, 20-fold, 50-fold or 100-fold higher than in a cell which is riot a brain cell. Preferably, this promoter is a human promoter. The expression cassette can also include an enhancer element for increasing the expression levels of exogenous protein to be expressed. Furthermore, the expression cassette can include polyadenylation sequences, such as the SV40 polyadenylation sequences or polyadenylation sequences of bovine growth hormone.

The viral vectors according to the invention can, preferably as part of one of their capsid proteins, comprise a peptide sequence of any of SEQ ID NO:1-5. Alternatively, variants of the amino acid sequence of SEQ ID NO:1-5 can be used, the same differing from the amino acid sequence of SEQ ID NO:1-5 by the modification of one amino acid. The modification can be a substitution, deletion or insertion of amino acids, as long as the variant retains the ability to mediate, as part of the capsid, the specific binding of the vector to the receptor structures of cells of the brain and/or spinal cord. The invention therefore also extends to variants of the sequence of SEQ ID NO:1-5 in which the C- or N-terminal amino acid has been changed. These variants have a sequence identity of more than 85% to the amino acid sequence shown in SEQ ID NO:1-5 when the sequences are compared using the programs GAP or BESTFIT. These computer programs for determining amino acid sequence identity are sufficiently known in the art.

The variant of the sequence of SEQ ID NO:1-5 can be based on the substitution of one amino acid—that is, one amino acid can be replaced with another amino acid. Preferably, the substitution by which the variants differ from one of the amino acid sequences in SEQ ID NO:1-5 is a conservative substitution, i.e., a substitution of one amino acid by an amino acid of similar polarity which gives the peptide similar functional properties. Preferably, the substituted amino acid is from the same group of amino acids as the amino acid which is used for the replacement. For example, a hydrophobic residue can be replaced with another hydrophobic residue, or a polar residue by another polar residue. Functionally similar amino acids which can be exchanged for each other by a conservative substitution include, for example, non-polar amino acids such as glycine, valine, alanine, isoleucine, leucine, methionine, proline, phenylalanine, and tryptophan. Examples of uncharged polar amino acids are serine, threonine, glutamine, asparagine, tyrosine, and cysteine. Examples of charged, polar (acidic) amino acids include histidine, arginine and lysine. Examples of charged, polar (basic) amino acids include aspartic acid and glutamic acid.

As variants of the amino acid sequences shown in SEQ ID NO:1-5 are regarded also those amino acid sequences in which an amino acid has been inserted. Such insertions can in principle be carried out as long as the resulting variant retains its ability to bind specifically to cells of the brain or spinal cord. In addition, in the present context, those proteins in which one of the two N-terminal amino acids of SEQ ID NO:2 is missing are considered to be variants of the amino acid sequence shown in SEQ. ID NO:1-5. This requires in turn that the correspondingly deleted variant binds specifically to cells of the brain or spinal cord.

Also encompassed by the invention are specific variants of the amino acid sequences shown SEQ ID NO:1-5 which were structurally modified at one amino acid, for example by introducing a modified amino acid. According to the invention, these modified amino acids can be amino acids that have been modified by biotinylation, phosphorylation, glycosylation, acetylation, branching and/or cyclization.

Viral vectors with capsids that comprise one of the peptide sequences according to the invention, or a variant thereof as defined above, specifically bind to cells of the brain and/or spinal cord. As used herein, a "specific" binding of the vectors according to the invention means that the vectors accumulate after systemic administration mainly on or in the cells of the brain and/or spinal cord. This means that more than 50% of the originally administered vector genomes accumulate in the area of the cells of the brain and/or spinal cord, while less than 50% accumulate in other cells or tissues (such as in the spleen or liver), or in the area thereof. It is preferred that more than 60%, 70%, 80%, 90%, 95%, or even more than 99% of the originally administered vector genomes accumulate in, or in the area of, the cells of the brain and/or spinal cord. Specific binding of the vectors can also be determined via the expression of the transgene. In the case of viral vectors which bind specifically to cells of the brain and/or spinal cord, more than 50% of the total expression of the transgene occurs in, or in the region of, the brain and/or spinal cord, while less than 50% of the expression can be observed in, or in the region of, other tissues. It is preferred, however, that more than 60%, 70%, 80%, 90%, 95%, or even more than 99% of the total measured expression of the transgene occurs in, or in the region of, the brain and/or spinal cord.

A person skilled in the art will easily be able to determine the specific binding of the vectors according to the invention to cells of the brain and/or spinal cord and the expression of the transgene introduced using the vectors. Methods for measuring the specificity of transduction and expression, suitable for this purpose, are shown in the examples below.

It is also preferable according to the invention that vectors whose capsids comprise variants of the amino acid sequences shown in SEQ ID NO:1-5 have at least about 50% of the binding activity of a corresponding viral vector whose capsid has the amino acid sequence shown in SEQ ID NO:1-5. It is even more preferred that the variants have about 60%, 70%, 80%, 90%, 95%, 96%, 97%, 98%, or 99% of the binding activity of a corresponding viral vector whose capsid has the amino acid sequence shown in SEQ ID NO:1-5. The binding activity of the vectors can be measured with the aid of in vitro assays, as described in the included examples.

Preferably, the binding activity of the vectors according to the invention, as can be determined by distribution of the vector genomes or expression of the transgene, for cells of the brain and/or spinal cord is at least 2-fold, 5-fold, 10-fold, 20-fold, 50-fold, 75-fold, 100-fold, 150-fold, 200-fold, 250-fold, 500-fold, 600-fold, 700-fold, 800-fold, 900-fold, 1000-fold, 2000 fold, 5000-fold, or 10,000-fold higher than the binding activity for a control cell which is not a cell of the brain or spinal cord (such as a spleen or liver cell).

The invention also relates to a cell that comprises a peptide, polypeptide or protein according to the invention, a nucleic acid encoding the same, a plasmid comprising such a nucleic acid, or a recombinant AAV vector as described above. It is preferably a human cell or cell line.

In one embodiment, a cell has been, for example, obtained from a human subject by biopsy and then transfected with the viral vector in an ex vivo procedure. The cell can then be reimplanted in the subject, or be supplied in other ways to the subject—for example by transplantation or infusion. The likelihood of rejection of transplanted cells is lower when the subject from which the cell was derived is genetically similar to the subject to which the cell is administered. Preferably, therefore, the subject to whom the transfected cells are supplied is the same subject from which the cells were previously obtained. The cell is preferably a human cell of the brain or spinal cord, particularly a neuronal cell, an endothelial cell of a blood vessel. The cell to be transfected can also be a stem cell, such as a human adult stem cell. It is particularly preferred according to the invention that the cells to be transfected are autologous cells that have been transfected ex vivo with the viral vector according to the invention, for example the recombinant AAV2 vector described above. The cells are preferably used in a method for treating a disorder or disease of the brain and/or spinal cord in a subject.

In another aspect, the invention relates to a method for producing an AAV vector in which a plasmid is used which encodes a capsid protein, the same comprising the amino acid sequence of SEQ ID NO:1 or a variant thereof. Alternatively, the vector can also comprise the amino acid sequence of SEQ ID NO:6, and in particular one of the amino acid sequences of SEQ ID NO:2-5 or a variant thereof. The basic method of producing recombinant AAV vectors comprising a transgene to be expressed is described in the prior art sufficiently [28]. HEK 293-T cells are transfected with three plasmids. A first plasmid comprises the cap and rep regions of the AAV genome, but the naturally occurring inverted repeats (ITRs) are missing. The cap region of this plasmid comprises a gene encoding at least one modified capsid protein, i.e., a gene which comprises the peptide sequence according to the invention. A second plasmid comprises a transgene expression cassette which is flanked by the corresponding ITRs, which constitute the packaging signal. The expression cassette is therefore packaged into the capsid in the course of the assembly of the viral particles. The third plasmid is an adenoviral helper plasmid, on which are encoded the helper proteins E1A, E1B, E2A, E4-orf6, VA, which are required for AAV replication in the HEK 293-T cells. Alternatively, it is also possible to produce the AAV vectors of the present invention in insect cells. A corresponding protocol is provided as an example in the below Example 6.

It was surprisingly found that the production of the recombinant vectors can influence their specificity. In the course of the present invention it was observed that vectors which have been produced in HEK293T cells using the protocol of Example 2 predominantly transfect endothelial cells of the blood vessels of the brain and spinal cord and only to a minor part neurons of the brain or the spinal cord. On the other hand, recombinant vectors which have been produced in Sf-9 cells using the protocol of Example 6 predominantly transfect neurons and to a much smaller extent endothelial cells. This observation can be used for further increasing the specificity of transfection.

Conditions which allow the accumulation and purification of the recombinant vectors according to the invention are known in the art. The vectors according to the invention can be purified, for example, by gel filtration processes—for example using a Sepharose matrix—desalinated, and subsequently purified by filtration. Other purification methods can further comprise a cesium chloride or iodixanol gradient ultracentrifugation process. Purification reduces potentially detrimental effects in the subject to which the adeno-associated viral vectors are administered. The administered virus is substantially free of wild-type and replication-competent virus. The purity of the virus can be checked by suitable methods such as PCR amplification.

In a further aspect, the invention provides a pharmaceutical composition comprising a viral vector of the present invention, particularly an AAV vector. The viral vector in this case is administered in a therapeutically effective amount to the patient, i.e., in an amount sufficient to considerably improve at least one symptom of the dysfunction or disease of the brain and/or spinal cord being treated, or to prevent the progression of the disease. A therapeutically effective amount of the viral vector of the present invention causes a positive change in one of said symptoms, i.e. a change which renders the phenotype of the afflicted subject more similar to the phenotype of a healthy subject that does not suffer from a disease of the brain and/or spinal cord.

In one preferred embodiment according to the invention, the administration of the viral vector occurs in an amount which leads to a complete or substantially complete healing of the dysfunction or disease of the brain and/or spinal cord. The pharmaceutical composition accordingly comprises a therapeutically effective dose of the vector according to the invention. A therapeutically effective dose will generally be non-toxic for the subject who undergoes the treatment.

The exact amount of viral vector which must be administered to achieve a therapeutic effect depends on several parameters. Factors that are relevant to the amount of viral vector to be administered are, for example, the route of administration of the viral vector, the nature and severity of the disease, the disease history of the patient being treated, and the age, weight, height, and health of the patient to be treated. Furthermore, the expression level of the transgene which is required to achieve a therapeutic effect, the immune response of the patient, as well as the stability of the gene product are relevant for the amount to be administered. A therapeutically effective amount of the viral vector can be determined by a person skilled in the art on the basis of general knowledge and the present disclosure.

The viral vector is preferably administered in an amount corresponding to a dose of virus in the range of $1.0 \times 10^{10}$ to $1.0 \times 10^{14}$ vg/kg (virus genomes per kg body weight), although a range of $1.0 \times 10^{11}$ to $1.0 \times 10^{13}$ vg/kg is more preferred, and a range of $5.0 \times 10^{11}$ to $5.0 \times 10^{12}$ vg/kg is still more preferred, and a range of $1.0 \times 10^{12}$ to $5.0 \times 10^{12}$ is still more preferred. A virus dose of approximately $2.5 \times 10^{12}$ vq/kg is most preferred. The amount of the viral vector to be administered, such as the AAV2 vector according to the invention, for example, can be adjusted according to the strength of the expression of one or more transgenes.

The viral vector of the present invention, such as the preferred AAV2 vector according to the invention, for example, can be formulated for various routes of administration—for example, for oral administration as a capsule, a liquid or the like. However, it is preferred that the viral vector is administered parenterally, preferably by intravenous injection or intravenous infusion. The administration can be, for example, by intravenous infusion, for example within 60 minutes, within 30 minutes or within 15 minutes. It is further preferred that the viral vector is administered locally by injection to the brain and/or spinal cord during a surgery. Compositions which are suitable for administration by injection and/or infusion typically include solutions and dispersions, and powders from which corresponding solutions and dispersions can be prepared. Such compositions will comprise the viral vector and at least one suitable pharmaceutically acceptable carrier. Suitable pharmaceutically acceptable carriers for intravenous administration include bacteriostatic water, Ringer's solution, physiological saline, phosphate buffered saline (PBS) and Cremophor EL™. Sterile compositions for the injection and/or infusion can be prepared by introducing the viral vector in the required amount into an appropriate carrier, and then sterilizing by filtration. Compositions for administration by injection or infusion should remain stable under storage conditions after their preparation over an extended period of time. The compositions can contain a preservative for this purpose. Suitable preservatives include chlorobutanol, phenol, ascorbic acid and thimerosal. The preparation of corresponding formulations and suitable adjuvants is described, for example, in "Remington: The Science and Practice of Pharmacy," Lippincott Williams & Wilkins; 21st edition (2005).

In a further aspect, the invention relates to a method for the therapeutic treatment of a disorder or disease of the brain and/or spinal cord, wherein a viral vector according to the invention, preferably an AAV vector as described above, is administered to a subject. The vector comprises a capsid which has at least one capsid protein containing the amino acid sequence of SEQ ID NO:1 or a variant thereof. Alternatively, the vector can also comprise an amino acid sequence of SEQ ID NO:6, in particular an amino acid sequence of SEQ ID NO:2-5 or a variant thereof. The viral vector further comprises a transgene, for example a therapeutic gene, which is useful for the treatment of the disorder or the disease of the brain and/or spinal cord. After administration to the subject being treated, preferably by systemic administration such as intravenous injection or infusion, for example, the vector brings about the specific expression of the gene in the cells of the brain and/or spinal cord.

7.: intravenous injection of the peptide library into the mouse.

FIG. 2 shows the sequences of the brain-specific peptides identified by means of the selection method. The peptide with the sequence shown in SEQ ID NO:1 was identified in the fourth round of selection.

FIG. 3 shows the gene expression after intravenous injection of recombinant AAV vectors into the living mouse. The luciferase expression was measured 14 days after systemic injection of $5 \times 10^{10}$ vector genomes using the IVIS® 200 Imaging System. A: vectors on the basis of the unmodified AAV2 wild-type capsid show gene expression predominantly in the liver. There is no measurable gene expression in the brain. In contrast, the recombinant AAV vector rAAV2-NRGTEWD (SEQ ID NO:1) induces a strong and specific gene expression in the brain.

Figure 4:
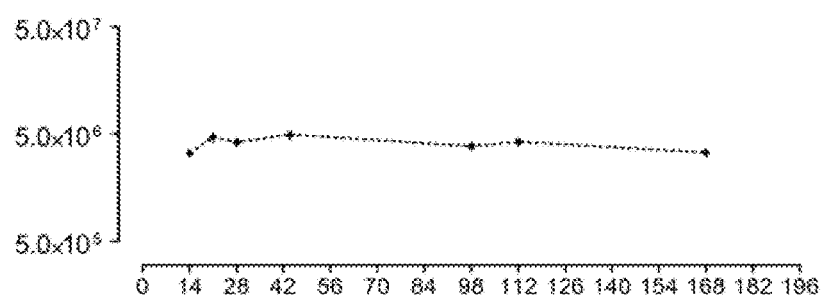

FIG. 4 shows a long-term expression analysis in mouse after systemic administration of recombinant rAAV2-NRGTEWD (SEQ ID NO:1) vector. Repeated measurements using the IVIS® 200 Imaging System exhibit stable gene expression in the brain over a period of 168 days (n=2).

Figure 5:
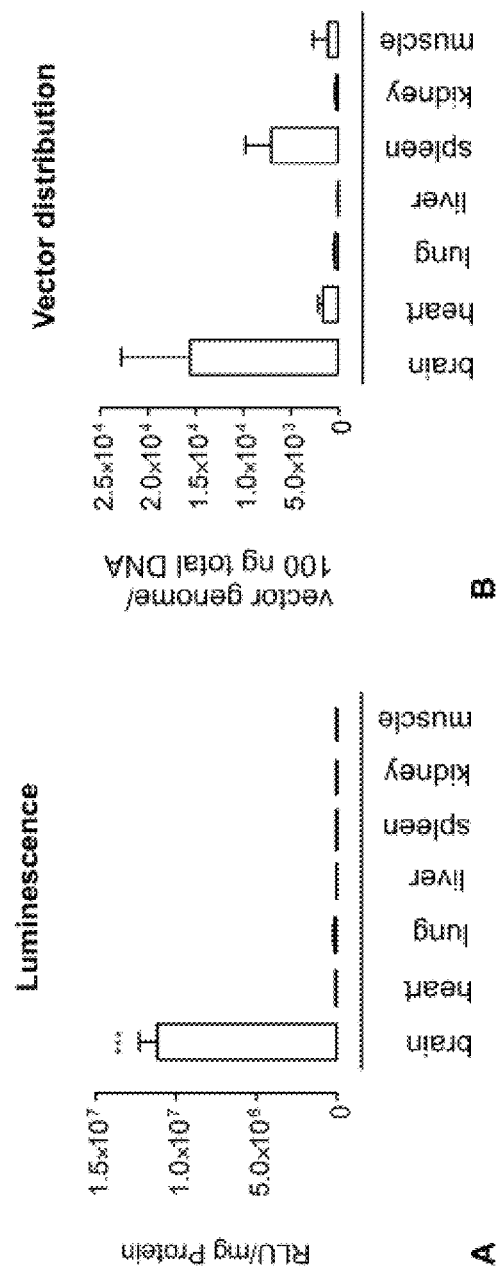

FIG. 5 shows the results of the determination of luminescence and vector 14 days after intravenous injection of $5 \times 1010$ vector genomes of the recombinant AAV vector rAAV2-NRGTEWD (SEQ ID NO:1). A: Measuring gene expression as bioluminescence in the lysates of different organs of the mouse showed a high specificity of the vector for the brain. B: Measuring the distribution of vector genomes in the lysates showed a significant accumulation of the vector in the brain. Mean values + standard deviation. Statistics were calculated by one-way ANOVA. $p<0.05=$*; $p<0.01=$; $p<0.001=$* for n=3.

EXAMPLES

All data was determined as mean values + standard deviation (SD). The statistical analysis was performed using the GraphPad Prism 3.0 program (GraphPad Software, San Diego, USA). Data was analyzed by one-way ANOVA followed by multiple comparison tests as per Bonferroni. P values>0.05 were considered significant.

Example 1: Selection of AAV2 Peptide Libraries

For the selection of tissue-specific AAV2 capsids, a random peptide library was prepared and selected in five rounds. A random $X_7$-AAV peptide library with a theoretical diversity of $1 \times 10^8$ individually occurring clones was prepared using a two-stage protocol as previously described [26-27]. A degenerate oligonucleotide was first produced which codes for seven randomized amino acids at nucleotide position 3967 in the AAV genome, which corresponds to the amino acid position R588 in VP1. The oligonucleotide had the sequence: 5'-CAGTCGGCCAGAGAGGC (NNK)$_7$GC-CCAGGCGGCTGACGAG-3' (SEQ ID NO:12). The second strand was produced using a Sequenase (Amersham, Freiburg, Germany) and the primer with the sequence 5'-CTCGTCAGCCGCCTGG-3' (SEQ ID NO:13). The double-stranded insert was cut with BglI, purified with the QIAquick Nucleotide Removal Kit (Qiagen, Hilden, Germany) and ligated into library plasmid pMT187-0-3 that had been digested with SfiI [26]. The diversity of the plasmid library was determined by the number of clones grown from a representative aliquot of transformed, electrocompetent DH5α bacteria on agar containing 150 mg/ml ampicillin. Library plasmids were harvested and purified by using the Plasmid Preparation Kit from Qiagen. The AAV library genomes were packaged into chimeric wild-type and library AAV capsids (AAV transfer shuttle) by transfecting $2 \times 10^8$ 293T cells in 10 cell culture dishes (15 cm) with the plasmid pVP3cm (containing the wild-type cap genes with modified codon usage without the inverted terminal repeats) [27], the library plasmids and the pXX6 helper plasmid [28], wherein the ratio between the plasmids was 1:1:2. The resulting AAV library transfer shuttles were used to infect $2 \times 10^8$ 293T cells in cell culture dishes (15 cm) with an MOI of 0.5 replication units per cell. Cells were superinfected with Ad5 (provided by the Laboratoire de Therapie Génigue, France), with an MOI of 5 plaque-forming units (pfu/cell). The final AAV display library was harvested from the supernatants after 48 hours. The supernatants were concentrated using VivaSpin columns (Viva Science, Hannover, Germany) and purified by iodixanol density gradient ultracentrifugation as previously described [29], and titrated by real-time PCR using the cap-specific primers 5'-GCAGTATGGTTCTGTATCTAC-CAACC-3' (SEQ ID NO:14) and 5'-GCCTG-GAAGAACGCCTTGTGTG-3' (SEQ ID NO:15) with the LightCycler system (Roche Diagnostics, Mannheim, Germany).

Figure 1:
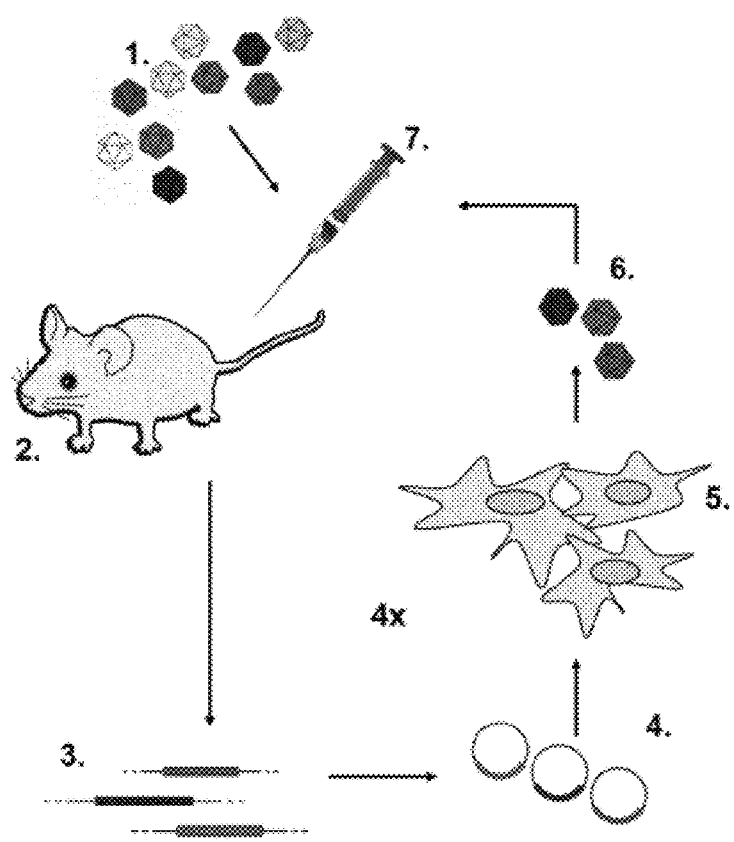
FIG. 1 shows the in vivo selection method of the AAV-peptide library used according to the invention.
1.: Randomized AAV peptide library with approx. $1 \times 10^8$ different capsid variants;
2.: Withdrawal of the target organ, 8 days after injection;
3.: DNA isolation and amplification of viral DNA fragments via real time PCR;
4.: Cloning into peptide library plasmids for sequencing and production of a secondary peptide library;
5.: Co-transfection of HEK2931 cells; production of a secondary peptide library;
6.: secondary AAV peptide library for further rounds of selection; contains pre-selected capsid variants.

For the in vivo selection $1 \times 10^{11}$ particles of the genomic library were injected into the tail vein of FVB/N mice. The particles were given 8 days for the distribution and the infection of the target cells. After 8 days, the mice were killed and the brains were removed. The total DNA of the tissue was extracted using the DNeasy Tissue Kit (Qiagen). The random oligonucleotides that were included in AAV particles of the library and had accumulated in the tissue of interest were amplified by nested PCR using the primers 5'-ATGGCAAGCCACAAGGACGATG-3' (SEQ ID NO:16) and 5'-CGTGGAGTACTGTGTGATGAAG-3' (SEQ ID NO:17) for the first PCR and the primers 5'-GGT-TCTCATCTTTGGGAAGCAAG-3' (SEQ ID NO:18) and 5-TGATGAGAATCTGTGGAGGAG-3' (SEQ ID NO:19) for the second PCR. The PCR-amplified oligonucleotides were used to prepare secondary libraries for three additional rounds of selection. The secondary libraries were generated like the primary libraries (see above), but without the additional step of producing transfer shuttles. The secondary plasmid library was used to transfect $2 \times 10^8$ 293T cells in cell culture dishes (15 cm) at a ratio of 25 library plasmids per cell, wherein the transfection reagent Polyfect (Qiagen) was used. After each round of selection, several clones were sequenced. The applied selection method is shown in FIG. 1.

Results: After five rounds of selection, several brain-binding capsids were selected. Capsids comprising the peptide sequences NRGTEWD (SEQ ID NO:1) were found to bind particularly strong to cells of the brain and spinal cord (see below). A further group of peptides, which also showed specificity for the brain and spinal cord comprised the peptide ADGVQWT (SEQ ID NO:2), DDGVSWK (SEC ID NO:3), SDGLTWS (SEQ ID NO:4) and SDGLAWV (SEQ ID NO:5). These peptides comprised the general motif XDGXXWX (SEQ ID NO:6). The peptides obtained in the various rounds of selection are shown in FIG. 2.

Example 2: Preparation and Quantification of Recombinant AAV Vectors in HEK293T Cells The clones enriched in Example 1 were produced as recombinant AAV vectors and tested for their transduction profile. Recombinant AAV vectors were produced by triple transfection of HEK293T cells. The cells were incubated at 37° C., 5% $CO_2$ in Dulbecco's modified Eagle Medium (Invitrogen, Carlsbad, USA), supplemented with 1% penicillin/streptomycin and 10% fetal calf serum. Plasmid DNA was transfected into 293T cells with the transfection agent Polyfect (Qiagen, Hilden, Germany). Four days after transfection, the cells were harvested and lysed, and the vectors were purified by means of iodixanol density gradient ultracentrifugation as previously described [29]. For the transfections, pXX6 was used as adenoviral helper plasmid [28], which encodes the luciferase gene pUF2-CMV-luc [27] or the GFP gene pTR-CMV-GFP [30], as was a plasmid encoding the AAV capsid of interest. The plasmids encoding the AAV capsid mutants which had been previously selected from the AAV library, and wild-type controls, were modified pXX2-187 [31] or pXX2 [28]. The inserts were processed as described into library inserts (see above). To quantify the recombinant vectors, the genomic titer was determined by the LightCycler system, as previously described [32], by real-time PCR using the CMV-specific primers 5'-GGCG-GAGTTGTTACGACAT-3' (SEQ ID NO:20) and 5'-GGGACTTTCCCTACTTGGCA-3' (SEQ ID NO:21).

Results: It was found that the yield with respect to virus titer for recombinant viruses with luciferase reporter gene was comparable to that of vectors which comprised a wild type AAV2 capsid which indicates that the accumulated peptides do not affect the assembly of the capsid or the packaging of the gene.

Example 3: Examination of the Tropism of the Recombinant AAV Vectors In Vivo

To be able to examine the tropism of the enriched peptides in vivo, the peptides were introduced into the capsid of a recombinant vector comprising a luciferase reporter gene. Vectors with mutated capsids were injected into mice along with control vectors. The AAV vectors were administered intravenously at a dose of $5\times10^{10}$ vector genomes (vg)/mouse (n=3 animals per injected AAV clone). On day 14, the animals were anesthetized with isoflurane. The luciferase expression was analyzed using a Xenogen IVIS200 Imaging System (Caliper Lifescience, Hopkinton, USA) with the Living Image 4.0 (Caliper) software, following intraperitoneal injection of 200 µl of luciferin substrate (150 mg/kg, Xenogen) per mouse. Representative, in vivo bioluminescence images of the expression of the transgene at different positions (ventral, dorsal, lateral) were taken when the luminescence in relative light units (photons/sec/cm$^2$) reached the highest intensity.

Then the animals were sacrificed, the organs of interest were removed quickly, and images of the expression of the transgene in individual organs were immediately taken. The organs were then frozen in liquid nitrogen and stored at −80° C. To quantify the luciferase expression, the organs were homogenized in reporter lysis buffer (RLB, Promega, Madison, USA). The determination of the luciferase reporter gene activity was carried out in a luminometer (Mithras LB9 40, Berthold Technologies, Bad Wildbad, Germany) at 10-second intervals after the addition of 100 µl luciferase assay reagent (LAR, Promega), with a 2-second delay between each of the measurements. The values were normalized in each sample with respect to the total amount of protein using the Roti NanoQuant protein assay (Roth, Karlsruhe, Germany).

Results: The in vivo measurement of bioluminescence after 14 days showed that the peptide NRGTEWD (SEC ID NO:1) led to an expression of the transgene in the brain ($\leq 10^4$ p/sec/cm$^2$/r). These results were confirmed by the control experiments carried out ex vivo with explanted organs. A randomly selected control clone of the non-selected library (CVGSPCG) (SEQ ID NO:43) led to a weak gene expression that occurred primarily in the heart and in some parts of the abdomen, but not in the brain (not shown). Wild-type AAV2 caused a weak gene expression in the heart, liver and skeletal muscle, but not in the brain (FIG. 3A).

The examination of the luciferase activity of tissue lysates from representative organs revealed that the vectors which comprised the brain-specific NRGTEWD (SEQ ID NO :1) capsid led to a strong and specific gene expression in the brain ($1.1\times10^7$ RLU/mg protein, see FIG. 5A). In other organ tissues, the NRGTEWD (SEQ ID NO:1) luciferase vector hardly showed expression.

The results further showed that The brain-specific expression of the transgene mediated by the NRGTEWD (SEQ ID NO:1) vector remained organ-specific over a long period. After intravenous administration of the AAV2 NRGTEWD (SEQ ID NO:1) luciferase vectors, the expression of the transgene was measured over a period of 168 days. The radiation emitted in the brain region was determined quantitatively. Over the entire period of time, the expression of the transgene was stable at a high level, and was limited to the brain (FIG. 4).

Example 4: Analysis of the Vector Distribution

In order to check whether the brain-specific expression of the transgene of intravenously injected NRGTEWD (SEQ ID NO:1) vectors is based on a specific homing, first the distribution of vectors was investigated 14 days after intravenous administration of $5\times10^{10}$ gp/mouse. The quantification of the vector genomes was performed by real-time PCR. First, the total DNA was extracted from the organ concerned at various time points after intravenous administration of $5\times10^{10}$ vg/mouse using a tissue homogenizer (Precellys 24, Peqlab, Erlangen, Germany) and the DNeasy Tissue Kit (Qiagen, Hilden, Germany) according to the manufacturer's instructions. The DNA was quantified using a spectrophotometer (NanoDrop ND-2000C, Peqlab). The analysis of the AAV vector DNA in the tissues was performed by quantitative real-time PCR using the above-described CMV-specific primer, wherein 40 ng of template were used, normalized with respect to the total DNA.

Results: The quantification of the vector genomes by real-time PCR showed a brain-specific homing of NRGTEWD (SEQ ID NO:1). The amount of vector genomes which could be detected in the brain ($1.6\times 10^4 \pm 7.1\times 10^3$ vg/100 ng total DNA) was significantly higher than the amount of vector genomes which was detected in another organ (FIG. 5B). To determine the direct correlation between vector homing and expression of the transgene, the vector distribution of wild-type AAV2, the control peptide CVGSPCG and the brain-specific peptide NRGTEWD (SEQ ID NO:1) was measured 14 days after intravenous administration of $5\times10^{10}$ gp/mouse, i.e., at the time when the expression of the transgene was determined (see above). The genomes provided by wild-type AAV2 vectors were mainly recovered from the liver and spleen, and the genomes of vectors which had the control peptide were obtained largely from the spleen (data not shown). In total, the amount of vector genomes which were detected in the spleen were relatively equal in all examined capsid variants, suggesting a non-specific capture mechanism for the particles in the reticulo-endothelial system which is independent of the provision and the expression of the transgene. In contrast, the distribution data of genomes which were provided by vectors which had the brain-specific peptide NRGTEWD (SEQ ID NO:1) was highly similar to the expression data of the transgene, with a highly specific accumulation observed in the brain. The amount of vectors detected in the brain which showed the peptide NRGTEWD (SEQ ID NO:1) was about 168-fold higher than in brains, which were injected with a wild-type vector or a control capsid vector. Overall, this data indicates that a brain-specific expression of the transgene, mediated by NRGTEWD (SEQ ID NO:1) vectors, is achieved by a tissue-specific homing of circulating particles.

Example 5: Immunohistochemistry and Histology

Immunohistochemistry was used to visualize the expression of the transgene at the cellular level in the brain, as well as in a control organ, 14 days after the intravenous administration of the rAAV-GFP vector having the peptide NRGTEWD (SEQ ID NO:1) and/or the wild-type AAV capsid as control. The brains of the animals were fixed with 4% (w/v) paraformaldehyde. The tissues were embedded in paraffin. Sections with a thickness of 2 μm were removed from wax, rehydrated and used for immunohistochemistry. An immunohistochemical procedure was performed using polyclonal antibodies for GFP (A-11122, Invitrogen) or CD31 (AB28364, Abcam, Cambridge, USA). The activity of the endogenous peroxidase was inactivated with 1% $H_2O_2$ in methanol for 30 minutes. Prior to staining with CD31, the sections were heated in citrate buffer (pH 6.0) for 20 minutes at 100° C. After washing in PBS, the sections were incubated for 30 minutes with PBS, 10% goat serum (Vector Lab, Burlingame, USA) and 2% milk powder (Roth). Primary antibodies were allowed to bind for 1 hour at 37° C. After washing in PBS, the sections were incubated for 30 minutes with a secondary, biotinylated goat anti-rabbit antibody (Vector Lab). Bound antibodies were visualized by using the VECTASTAIN-Elite ABC kit (Vector Lab) and 3,3'-diaminobenzidene (DAB, Sigma-Aldrich, St. Louis, USA). Selected sections were counterstained with Hemalum.

Results: In the brains of mice injected with rAAV-NRGTEWD (SEQ ID NO:1), a microscopic examination showed intensive staining of the endothelial cells over the entire microvasculature and to a slightly lesser extent in the large vessels (data not shown). In contrast, brain tissue of mice which was injected with wild-type AAV2 vector showed no staining. To confirm the tissue specificity, the liver was analyzed as a control organ (a tissue which is known to frequently demonstrate high expression of a transgene after injection of wild-type AAV2 vector). In the liver, hepatocyte staining was observed after administration of wild-type rAAV2 vector; but no staining was observed after administration of rAAV2-NRGTEWD (SEQ ID NO:1) vector. The endothelial lineage of cells transduced with the vectors was confirmed by CD31 staining, wherein the pattern obtained by the GFP staining was confirmed in serial sections of the brains of mice injected with rAAV2-NRGTEWD(SEQ ID NO:1) (data not shown).

The examination of the spinal cord of mice which have been injected with rAAV-NRGTEWD (SEQ ID NO:1) also revealed an intensive staining of the endothelial cells of the microvasculature which shows that not only the endothelial cells of the brain but rather the endothelial cells of the complete central nervous system are transducable with the peptides of the invention (data not shown).

Example 6: Production and Quantification of Recombinant AAV Vectors Using the Baculovirus Expression System in Sf9 Insect Cells.

For the production of recombinant AAV vectors in Sf9 insect cells [33-35] the modified AAV2 genome having the oligonucleotide insert in the cap gene which encodes the peptide insertion (see above) was cloned into the donor plasmid pFASTBAC Dual (Life Technologies, Darmstadt, Germany). In addition, an artificial intron was inserted into the donor plasmid which included the polh promoter, thereby giving plasmid pFBD-Rep$_{in}$/Cap$_{in}$ [35]. For establishing the donor plasmid pFB-CAG-eGFP, the CAG promoter and the eGFP gene were cloned together with the SV40 polyadenylation signal and the AAV2 ITRs into plasmid pFASTBAC1 (Life Technologies). The donor plasmids were used for transforming DH10Bac E. coli cells which were subsequently used for isolating recombinant bacmids that comprised the recombinant AAV genome or the eGFP transgene cassette, respectively. The bacmids (9 μg) were used for transfection of $1 \times 10^6$ Sf9 cells using the Fectofly-Transfektionreagenz (Poly-plus Transfection/VWR International GmbH, Darmstadt, Germany) in a 6-well format. After 3 days of incubation of the transfected Sf9 insect cells at 27° C. in insect X-Press Medium (Lonza, Cologne, Germany) with 1% Gentamycin (Lonza), 500 μl of the recombinant baculoviruses present in cell culture supernatants were used for the amplification of $2.5 \times 10^7$ fresh Sf9 cells in T175 cell culture flasks for additional 3 days at 27° C. in Insect X-Press Medium (Lonza) with 1% Gentamycin. The baculoviruses amplified in this way were used for infecting fresh Sf9 cells for producing recombinant AAV vectors. For this purpose, recombinant baculovirus with inserted AAV genome and recombinant baculovirus with inserted eGFP transgene cassette were mixed and used together in 400 ml Insect X-Press Medium with 1% Gentamycin in a 1 L Erlenmeyer flask for infecting $6 \times 10^8$ insect cells. The cells were subsequently incubated at 27° C. under agitation (110 rpm). 4 days after infection, the cells were harvested, lysed, and the AAV vectors were purified via iodixanol gradient ultra centrifugation as described before [29]. For quantification of the recombinant vectors, the genomic titer was determined by quantitative real time PCR using the CMV specific primer of SEQ ID NO:20 and SEQ ID NO:21 in the LightCycler system as described before [32].

Results: By using the baculovirus expression system, higher titers of recombinant AAV vectors were achieved in Sf9 insect cells compared to the production in HEK293T cells after triple transfection. While the yield of virus production in HEK293T cells had a maximum of $1.9 \times 10^4$ genomic particles per cell, a yield of up to $7.9 \times 10^4$ genomic particles per cell were observed in Sf9 insect cells. It could further be observed that rAAV2-NRGTEWD (SEQ ID NO:1) vectors produced in Sf9 insect cells had a higher affinity for neurons than comparable recombinant vectors, which have been produced in HEK293T cells (data not shown). Thus, the choice of the specific production process for the recombinant vectors provides the possibility of increasing the specificity of the vectors for the neuron or endothelial cells, respectively.

READINGS

[1] Tenenbaum et al., 2003, Curr Gene Ther, 3:545-565
[2] Work et al., 2006, Mol Ther, 4:683-693
[3] Shi et al., 2006, Hum Gene Ther, 17:353-361
[4] US 2007/0172460 A1
[5] Michelfelder et al., 2009, PLOS One, 4(4):e5122
[6] Kaplitt et al., 2007, Lancet, 369(9579): p. 2097-105
[7] Gray et al., 2010, Mol Ther, 18(3): p. 570-8
[8] Shevtsova et al., 2005, Exp Physiol. 90(1): p. 53-9
[9] Gray et al., 2011, Hum Gene Ther, 22(9): p. 1143-53

[10] Aebischer et al., 1996, Nat Med, 2(6): p. 696-9
[11] McCown et al., 1996, Brain Res, 713(1-2): p. 99-107
[12] During et al., 1998, Gene Ther. 5(6): p. 820-7
[13] Nagabhushan Kalburgi et al., 2013, Discov Med, 15(81): p. 111-9
[14] Alonso et al., 2013, Mol Ther Nucleic Acids, 2: p. e73
[15] Shi and Bartlett, 2003, Mol Ther, 7:515-525
[16] Loiler et al., 2003, Gene Ther, 10:1551-1558
[17] Rabinowitz et al., 1999, Virology, 265:274-285
[18] Wu et al., 2000, J Virol, 74:8635-8647
[19] Shi et al., 2001, Hum Gene Ther, 12:1697-1711
[20] Warrington et al., 2004, J Virol, 78:6595-6609
[21] Girod et al., 1999, Nat Med, 5:1052-1056
[22] Grifman et al., 2001, Mol Ther, 3:964-975
[23] Opie et al., 2003, J Virol, 77:6995-7006
[24] Kern et al., 2003, J Virol, 77:11072-11081
[25] Russell et al., 1998, J Virol, 72:309-319)
[26] Muller et al., 2003, Nat Biotechnol 21, 1040-1046
[27] Waterkamp, et al., 2006, J Gene Med 8, 1307-1319
[28] Xiao et al., 1998, Journal of Virology 72, 2224-2232
[29] Zolotukhin, et al., 1999, Gene Ther 6, 973-985
[30] McCarty et al., 2001, Gene Ther 8, 1248-1254
[31] Michelfelder, et al., 2007, Exp Hematol 35, 1766-1776
[32] Rohr et al., 2005, J Virol Methods 127, 40-45
[33] Urabe et al., 2002, Hum Gene Ther 13, 1935-1943
[34] Kohlbrenner et al., 2005, Mol Ther 12, 1217-1225
[35] Chen, 2008, Mol Ther 16, 924-930 (2008)

The invention claimed is:

1. A capsid protein of a viral vector characterized in that it comprises the amino acid sequence of SEQ ID NO:1.

2. The capsid protein according to claim 1, which is a capsid protein of an adeno-associated virus (AAV).

3. The capsid protein according to claim 2, which is a capsid protein of an AAV of a serotype selected from the group consisting of serotypes 2, 4, 6, 8, and 9.

4. The capsid protein according to claim 3, which is a capsid protein of an AAV of serotype 2.

5. The capsid protein according to claim 4, which is a VP1 protein of an AAV of serotype 2.

6. The capsid protein according to claim 1, comprising the amino acid sequence of SEQ ID NO:10.

7. A cell which comprises a capsid protein according to claim 6.

8. A pharmaceutical composition which comprises a capsid protein according to claim 6.

9. A method for the targeted delivery of viral vectors to the brain and/or spinal cord in a subject, comprising administering a capsid protein according to claim 6 to the subject.

10. A viral capsid which comprises the capsid protein according to claim 1.

11. A cell which comprises a capsid protein according to claim 1.

12. A pharmaceutical composition which comprises a capsid protein according to claim 1.

13. A method for the targeted delivery of viral vectors to the brain and/or spinal cord in a subject, comprising administering a capsid protein according to claim 1 to the subject.

14. A nucleic acid which encodes a capsid protein characterized in that the capsid protein comprises the amino acid sequence of SEQ ID NO:1.

15. A plasmid which comprises a nucleic acid according to claim 14.

16. The nucleic acid of claim 14, characterized in that the capsid protein comprises the amino acid sequence of SEQ ID NO:1.

17. A recombinant viral vector which comprises a capsid and a transgene packaged therein, wherein the capsid comprises at least one capsid protein, characterized in that the capsid protein comprises the amino acid sequence of SEQ ID NO:1.

18. The recombinant viral vector according to claim 17, which is a recombinant AAV vector.

19. The recombinant viral vector according to claim 18, which is an AAV vector of a serotype selected from the group consisting of serotypes 2, 4, 6, 8, and 9.

20. The recombinant viral vector according to claim 19, which is an AAV vector of serotype 2.

21. The recombinant viral vector according to claim 17, wherein the transgene encodes one of the following proteins: a membrane or tight junction protein, a neuraminidase, glucuronidase, a chemokine antagonist, neurotrophic factor of glia cells (GDNF), neprilysine, cholesterol 24 hydroxylase, aromatic L-amino acid decarboxylase, a tyrosine hydroxylase, GTP cyclohydrolase I, and survival of motor neuron (SMN) protein.

22. The recombinant viral vector according to claim 21, wherein the transgene encodes a neuraminidase.

23. The recombinant viral vector according to claim 21, wherein said membrane or tight junction protein is a claudin or occludin.

24. The recombinant viral vector according to claim 21, wherein said neuraminidase is neuraminidase 1.

25. The recombinant viral vector according to claim 21, wherein said chemokine antagonist is CCL2-7ND.

26. The recombinant viral vector according to claim 17, wherein the transgene is in the form of an ssDNA or a dsDNA.

27. A method for the targeted delivery of viral vectors to the brain and/or spinal cord in a subject, comprising administering a recombinant viral vector according to claim 17 to the subject.

28. The method according to claim 27, wherein the subject is a mammal.

29. The method according to claim 28, wherein the mammal is a human.

30. The method according to claim 27, wherein the vector is formulated for intravenous administration.

31. A pharmaceutical composition which comprises a viral vector according to claim 17.

32. A recombinant viral vector which comprises a capsid and a transgene packaged therein, wherein the capsid comprises at least one capsid protein, characterized in that the capsid protein comprises the amino acid sequence of SEQ ID NO:10.

33. The recombinant viral vector according to claim 32, which is an AAV vector of serotype 2.

34. The recombinant viral vector according to claim 32, wherein the transgene encodes one of the following proteins: a membrane or tight junction protein, a neuraminidase, glucuronidase, a chemokine antagonist, neurotrophic factor of glia cells (GDNF), neprilysine, cholesterol 24 hydroxylase, aromatic L-amino acid decarboxylase, a tyrosine hydroxylase, GTP cyclohydrolase I, and survival of motor neuron (SMN) protein.

35. The recombinant viral vector according to claim 34, wherein the transgene encodes a neuraminidase.

36. The recombinant viral vector according to claim 34, wherein said membrane or tight junction protein is a claudin or occludin.

37. The recombinant viral vector according to claim 34, wherein said neuraminidase is neuraminidase 1.

38. The recombinant viral vector according to claim 34, wherein said chemokine antagonist is CCL2-7ND.

39. The recombinant viral vector according to claim 32, wherein the transgene is in the form of an ssDNA or a dsDNA.

40. A method for the targeted delivery of viral vectors to the brain and/or spinal cord in a subject, comprising administering a recombinant viral vector according to claim 32 to the subject.

41. The method according to claim 40, wherein the subject is a mammal.

42. The method according to claim 40, wherein the mammal is a human.

43. The method according to claim 40, wherein the vector is formulated for intravenous administration.

44. A pharmaceutical composition which comprises a viral vector according to claim 32.

* * * * *